United States Patent
Hedrich et al.

(10) Patent No.: US 11,047,846 B2
(45) Date of Patent: Jun. 29, 2021

(54) GAS SENSOR FOR DETERMINING THE EXPIRATORY $CO_2$ CONTENT OF RESPIRATORY AIR

(71) Applicants: Hahn-Schickard-Gesellschaft fuer angewandte Forschung e.V., Villingen-Schwenningen (DE); GS Elektromedizinische Geräte G. Stemple GmbH, Kaufering (DE)

(72) Inventors: Frank Hedrich, Villingen-Schwenningen (DE); Gerhard Kattinger, St. Georgen (DE); Matthias Storz, Trossingen (DE); Rolf Bronner, Baden-Baden (DE); Sophie Billat, Villingen-Schwenningen (DE)

(73) Assignees: Hahn-Schickard-Gesellschaft fuer angewandte Forschung e.V., Villingen-Schwenningen (DE); GS Elektromedizinische Geräte G. Stemple GmbH, Kaufering (DE)

( * ) Notice: Subject to any disclaimer, the term of this patent is extended or adjusted under 35 U.S.C. 154(b) by 0 days.

(21) Appl. No.: 16/789,873

(22) Filed: Feb. 13, 2020

(65) Prior Publication Data
US 2020/0232971 A1    Jul. 23, 2020

Related U.S. Application Data

(63) Continuation of application No. PCT/EP2018/071838, filed on Aug. 10, 2018.

(30) Foreign Application Priority Data

Aug. 14, 2017  (EP) .................................. 17186145

(51) Int. Cl.
*G01N 33/497* (2006.01)
*G01F 1/76* (2006.01)
(Continued)

(52) U.S. Cl.
CPC ............. *G01N 33/497* (2013.01); *G01F 1/76* (2013.01); *G01K 15/005* (2013.01);
(Continued)

(58) Field of Classification Search
CPC ...... G01N 33/497; G01N 25/00; G01N 33/00; G01F 1/76; G01K 15/005; G01L 19/0092
(Continued)

(56) References Cited

U.S. PATENT DOCUMENTS 5,177,696 A * 1/1993 Bonne ................. G01N 25/005
                                                          374/44
7,913,542 B2 * 3/2011 Pendergrass ....... G01N 33/0009
                                                          73/31.05
(Continued)

FOREIGN PATENT DOCUMENTS

DE  102010047159 A1  4/2012
JP      2007519930 A   7/2007
(Continued)

OTHER PUBLICATIONS

Kliche et al. "Sensor for Thermal Gas Analysis Based on Micromachined Silicon-Microwires." IEEE Sensors Journal, vol. 13, No. 7, Jul. 2013, pp. 2626-2635. accessed Sep. 30, 2020 from IEEEXplore.*
(Continued)

*Primary Examiner* — Nimeshkumar D Patel
*Assistant Examiner* — Jean F Morello
(74) *Attorney, Agent, or Firm* — Michael A. Glenn; Perkins Coie LLP

(57) ABSTRACT

The invention relates to a sensor arrangement having a barometric pressure sensor and a thermal gas sensor, wherein the thermal gas sensor is arranged on the barometric pressure sensor or beside the barometric pressure sensor such that a gas-permeable measurement structure of the thermal gas sensor is arranged in front of a gas inlet opening
(Continued)

of the barometric pressure sensor or in front of a pressure-sensitive surface of the barometric pressure sensor.

21 Claims, 20 Drawing Sheets

(51) Int. Cl.
    *G01K 15/00*     (2006.01)
    *G01L 19/00*     (2006.01)
    *G01N 25/00*     (2006.01)
    *G01N 33/00*     (2006.01)

(52) U.S. Cl.
    CPC .......... *G01L 19/0092* (2013.01); *G01N 25/00* (2013.01); *G01N 33/004* (2013.01)

(58) Field of Classification Search
    USPC .......................................... 73/23.3
    See application file for complete search history.

(56) References Cited

U.S. PATENT DOCUMENTS

| | | | |
|---|---|---|---|
| 10,247,690 B2 * | 4/2019 | Bourlon | G01N 33/0004 |
| 10,788,388 B2 * | 9/2020 | Soshino | G01L 9/0041 |
| 2011/0009764 A1 | 1/2011 | Lanier et al. | |
| 2012/0318058 A1 * | 12/2012 | Kimura | G01F 1/6845 |
| | | | 73/204.23 |
| 2014/0036953 A1 | 2/2014 | Kimura et al. | |
| 2015/0238722 A1 * | 8/2015 | Al-Ali | A61M 16/085 |
| | | | 128/205.13 |
| 2015/0327807 A1 * | 11/2015 | Bronner | A61B 5/486 |
| | | | 600/531 |
| 2016/0202200 A1 | 7/2016 | Nakano et al. | |
| 2017/0176405 A1 | 6/2017 | Pretre et al. | |
| 2017/0191895 A1 * | 7/2017 | Eckhardt | G01L 19/147 |
| 2018/0120245 A1 * | 5/2018 | Dill | A61B 5/082 |
| 2020/0049539 A1 * | 2/2020 | De Luca | G01L 9/0054 |

FOREIGN PATENT DOCUMENTS

| | | |
|---|---|---|
| JP | 2015045515 A | 3/2015 |
| JP | 2015227880 A | 12/2015 |
| WO | 2005073716 A1 | 8/2005 |

OTHER PUBLICATIONS

"Distributed thermal micro sensors for fluid flow", Distributed thermal micro sensors for fluid flow, Universiteit Twente, (Nov. 13, 2002), ISBN 978-90-36-51828-4, XP055524493, 2002.

Kliche et al., Sensor for Thermal Gas Analysis Based on Micromachined Silicon-Microwires, IEEE Sensors Journal, Jul. 2013, vol. 13, No. 7, 2626-2635, Jul. 2013.

* cited by examiner

During expiration: $CO_2$ concentration in exhaled air of the patients Diffusion of the $CO_2$ molecules through bacteria filter (as an example: with 1 μm mesh size, a diffusion time of 7.2 ms is needed for a concentration leap to 5 vol% at the sensor).

illustration of the integration of the $CO_2$ sensor parameters influencing the diffusion according to Fick's Law:
expired air
external Air
channel
sensor's chamber
filter
porosity
sensor
diffusion of gasses through the filter metal oxide sensors (MOX)

electrochemical potentiometric sensors (NASICON)

non-dispersive infrared sensor (NDIR)

top view

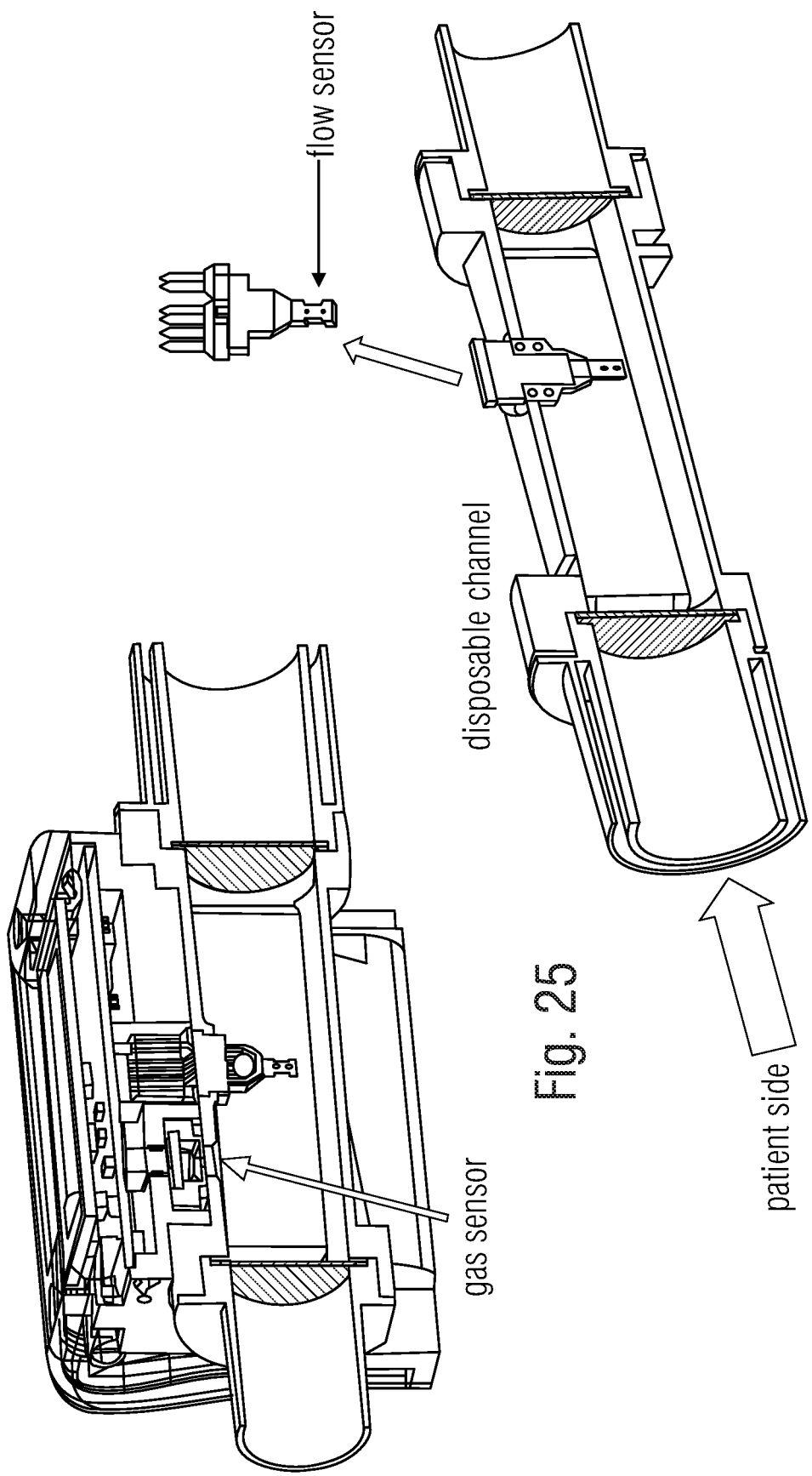

GAS SENSOR FOR DETERMINING THE EXPIRATORY CO₂ CONTENT OF RESPIRATORY AIR

CROSS-REFERENCE TO RELATED APPLICATIONS

This application is a continuation of copending International Application No. PCT/EP2018/071838, filed Aug. 10, 2018, which is incorporated herein by reference in its entirety, and additionally claims priority from European Application No. EP 17186145.3, filed Aug. 14, 2017, which is also incorporated herein by reference in its entirety.

The present application relates to a sensor arrangement, a sensor apparatus as well as to a method for producing a sensor arrangement, in particular to sensor arrangements, sensor apparatuses and production methods for a sensor arrangement for determining an expiratory $CO_2$ content of respiratory air.

BACKGROUND OF THE INVENTION

Sensor arrangements or sensor apparatuses can be used for performing respiratory air analysis, for example in medical diagnostics. The $CO_2$ content in the exhaled air of a patient is, for example, an important measurement parameter in anesthetics.

Conventional $CO_2$ sensors, so-called capnometers mainly use infrared spectroscopic measurement methods measuring absorption of $CO_2$ molecules. These so-called non-dispersive infrared sensors (NDIR) measure the concentration of $CO_2$ in breathing gas by an absorption measurement, more accurately an infrared absorption at 4.3 μm wavelength. Such sensors are non-consumptive and allow measurement in the main stream. Their mode of operation necessitates a respectively precise structure and includes expensive optical components. The used components are very sensitive against contamination by secretions and respiratory humidity and the used photodiode is subject to an aging process.

Further, so-called metal oxide sensors (MOX) are used, the same use a chemical reaction of a thin layer and have a high sensitivity at small concentrations. These sensors are inexpensive, however, a disadvantage is that the sensor is consumed during operation and has no long-term stability. Also, the selectivity regarding the type of gas is low and such sensors are not suitable for $CO_2$. Since the operating temperature is at up to 800° C., the usage in the main stream is risky.

So-called electrochemical potentiometric sensors (NASICON) have a high accuracy at small dimensions. However, it is a disadvantage that the electrode material is consumed and these sensors are comparatively expensive with a short life span.

Further, microelectromechanical wire sensors, so-called "MEMS" wire sensors needing only little installation space exist. Due to their physical measurement principle, the same are non-consumptive and are inexpensive to produce. It is also an advantage that measurement is possible in the steadied main stream. It is a disadvantage that such sensors offer no real gas analysis, rather, the gas components have to be known. Also, the thermal resolution is limited and is at 0.2 vol % $CO_2$.

In order to perform measurements directly at the patient, so-called point-of-care measurements, different portable devices for breathing gas analysis exist. A portable capnograph for $CO_2$ measurement for evaluation operating with an infrared sensor is, for example, offered by Weinman Diagnostics. Connection to the patient takes place via a nasal cannula and the exhaled air is guided in the side stream through a long tube to the device for determining the $CO_2$ content.

Further, different systems for patient respiration exist, the same are differentiated depending on the use in the clinical or home-care field. These systems can include measurement means for determining pressure, breathing flow and breathing gas analysis, for this several devices have to be combined that mostly measure remote from the patient. Therefrom, it can be derived that an inexpensive measurement of respiratory flow and $CO_2$ content close to the patient has not been implemented so far.

SUMMARY

According to an embodiment, a sensor arrangement may have: a barometric pressure sensor; and a thermal gas sensor; wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor; wherein the thermal gas sensor includes a frame that is arranged on the barometric pressure sensor and wherein the frame is configured to carry the gas-permeable measurement structure such that the active areas of the gas-permeable measurement structure span a free inner area of the thermal gas sensor surrounded by the frame; wherein the gas inlet opening of the barometric pressure sensor or the pressure-sensitive surface of the barometric pressure sensor borders on the free inner area of the barometric pressure sensor.

According to another embodiment, a sensor apparatus may have: a flow channel, wherein the flow channel includes an opening in a wall; and an inventive sensor arrangement, wherein the sensor arrangement is arranged such that the sensor arrangement is spatially connected to the inside of the flow channel through the opening to allow gas exchange between the inside of the flow channel and the sensor arrangement.

According to another embodiment, a sensor arrangement may have: a barometric pressure sensor; and a thermal gas sensor; wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor; wherein the thermal gas sensor includes a carrier material, wherein the thermal gas sensor includes a continuous recess in a central area extending from a surface of the thermal gas sensor facing away from the barometric pressure sensor up to a surface of the thermal gas sensor facing the barometric pressure sensor and wherein the gas-permeable measurement structure is arranged in an area of the recess.

According to another embodiment, a sensor arrangement may have: a barometric pressure sensor; and a thermal gas sensor; wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor; wherein the thermal gas sensor is connected to the barometric pressure sensor by means of an adhesive, such that the adhesive is not in contact with the gas inlet opening of the barometric pressure sensor or with the pressure-sensitive surface of the barometric pressure sensor.

According to another embodiment, a sensor arrangement may have: a barometric pressure sensor; and a thermal gas sensor; wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor; wherein the sensor arrangement includes a printed circuit board material; wherein the barometric pressure sensor and on top of the same the thermal gas sensor are arranged on one side of the printed circuit board material and wherein a plug or solder contact for electric contacting are arranged on another side of the printed circuit board material facing away from the pressure sensor and the thermal gas sensor, or wherein the barometric pressure sensor and on top of the same the thermal gas sensor are arranged in a recess of the printed circuit board material and wherein a plug for electric contacting is arranged on a side of the printed circuit board material.

According to a first embodiment, a sensor arrangement comprises a barometric pressure sensor and a thermal gas sensor, wherein the thermal gas sensor is arranged on the barometric pressure sensor or beside the barometric pressure sensor such that a gas-permeable measurement structure of the thermal gas sensor is arranged, for example, immediately in front of a gas inlet opening of the barometric pressure sensor or in front of a pressure-sensitive surface of the barometric pressure sensor. The pressure-sensitive surface of the pressure sensor can, for example, be a membrane and the gas-permeable measurement structure can be arranged immediately in front of the gas inlet opening or the pressure-sensitive surface.

This embodiment is based on the knowledge that it is advantageous to minimize the spatial distance between gas sensor and pressure sensor, which has the advantage that this reduces systematic measurement errors to a minimum since the measurement values of the gas sensor can depend on the pressure.

In a second embodiment, the thermal gas sensor comprises, for example as the gas-permeable measurement structure or part of the same, at least three electric conductor structures, for example wires or silicon wires, wherein the electric conductor structures are spaced apart by gaps. Of these conductor structures, a first electric conductor structure, for example a wire, is configured to be provided with a heating signal and second and third conductor structures, for example wires, are arranged asymmetrically with respect to the first conductor structure, e.g., such that a distance between the first wire and the second wire differs from the distance between the first and the third wire, for example by an arrangement on different sides of the first wire or on different sides beside the first wire. The second and third conductor structures are configured to operate as temperature sensors, such that, for example, a difference in the heat conduction through the gas or gas mixture between the first and the second wire and the heat conduction between the first and the third wire can be determined, such that based on the difference of the heat transfers, for example, the concentration of a proportion of the gas mixture can be inferred.

This embodiment is based on the knowledge that it is advantageous to use a gas sensor having three asymmetrically arranged conductor structures since the same can measure the thermal heat transfer in a very reliable manner.

In a third embodiment, the electric conductor structures, e.g., wires or heaters/detectors, are cantilevered, such that, for example, gas can reach the inlet opening of the barometric pressure sensor or the pressure-sensitive surface of the barometric pressure sensor, for example, through the gaps between the conductor structures, e.g. wires.

This embodiment is based on the knowledge that it is advantageous to cantilever the conductor structures since this has as little influence as possible on the mode of operation of the pressure sensor as there are no supporting structures.

In a fourth embodiment, the electric conductor structures are crystalline silicon wires, or in a further embodiment, the electric conductor structures are a polycrystalline heater on a membrane material as well as semiconductor temperature detectors or thermostacks. This embodiment is based on the knowledge that it is advantageous to select specific materials, such as crystalline silicon wires, as material for the electric conductor structures having a good electric and thermal conductivity, as well as a high temperature coefficient of resistance and, in comparison, to platinum wires, with filigree diameter and short conducting path length, a basic resistance that is advantageous for electric evaluation circuits that keeps the evaluation current and hence the thermal self-heating low in order to be able to perform gas measurement as fast as possible, i.e., without much delay.

In a fifth embodiment, the thermal gas sensor includes at least two electric conductor structures, wherein the electric conductor structures are spaced apart by at least one gap. Here, a first electric conductor structure is configured to be provided with a heating signal, wherein a second electric conductor structure is configured to operate as temperature sensor.

In a sixth embodiment, the sensor arrangement is configured to provide the first conductive structure with a heating signal in a first time interval and to use the second conductor structure as temperature sensor and further to provide the second conductor structure with a heating signal in a second time interval and to use the first conductor structure as temperature sensor.

In a seventh embodiment, the thermal gas sensor includes, for example, at least three electrically conductive ridges as gas-permeable measurement structure or part of the same, wherein the ridges are spaced apart by gaps, and wherein a metallization or doping of the first ridge is provided with a heating signal and second and third ridges are arranged asymmetrically with respect to the first ridge, for example on different sides of the first ridge or on different sides beside the first ridge, and wherein metallizations or dopings of the second and third ridge are configured to operate as temperature sensors.

This embodiment is based on the finding that it is advantageous to use ridges as conductor structures since the same are mechanically resistant and hence offer a good tradeoff between robustness and minimum interference of the pressure sensor.

In an eighth embodiment, the electric conductor structures or wires or ridges are surrounded by a gas to be analyzed, wherein the first electric conductor structure or the first wire or the first ridge is configured to allow heat transfer via the gas to be analyzed, e.g., a gas mixture, to the second electric conductor structure, the second wire or the second ridge and to the third electric conductor structure or the third wire or ridge and wherein the second and third electric conductor structures, wires or ridges are configured to serve as sensors for the heat transfer, for example by an evaluation means.

This embodiment is based on the knowledge that it is advantageous to perform gas measurement by means of heat transfer since this allows reliable non-corrosive and fast measurement of gas proportions in a gas mixture.

In a ninth embodiment, the heating signal is provided as a periodic heating signal. In contrary to static heat excitation, in periodic operation, a further gas parameter, e.g., apart from heat conductivity, the temperature conductivity of the gas can be extracted. The temperature conductivity of gas can, for example, be determined as follows:

$$a = \frac{\lambda}{\rho * c_p}$$

wherein $\lambda$ corresponds to the heat conductivity, $\rho$ to the density and $c_p$ to the heat capacitance.

This embodiment is based on the knowledge that the usage of a periodic heating signal allows performing the measurement at the gas to be analyzed very fast with a good time resolution, such that it is possible, for example, to measure the $CO_2$ content of a gas mixture in a time-resolved manner and/or with high accuracy.

In a tenth embodiment, the thermal gas sensor comprises a carrier material, such as a substrate like silicon. The carrier material can be a layer material that is arranged, for example, on the barometric pressure sensor. In this embodiment, the thermal gas sensor has a continuous recess, for example a hole, in a central area extending from a surface facing away from the pressure sensor up to a surface of the gas sensor facing the barometric pressure sensor, for example the carrier material, and wherein the gas-permeable measurement structure is arranged in an area of the recess, for example in the recess or, seen from the pressure sensor, in an upper boundary of the recess and comprises, e.g., the cantilevered heater or heating wire and the cantilevered detectors or detector wires/detector elements.

This embodiment is based on the knowledge that it is advantageous to arrange the thermal gas sensor in immediate proximity to the active area of the pressure sensor, such that the thermal gas sensor performs the gas measurement practically at the same location where pressure and the gas temperature are measured by the pressure sensor, whereby systematic errors in the measurement values or the measurement value consideration can be eliminated.

In an eleventh embodiment, the thermal gas sensor comprises a frame that is arranged on the barometric pressure sensor, wherein the frame is configured to carry the gas-permeable measurement structure, such that the active areas, such as wires or cantilevered silicon wires, cantilevered bridge structures, such as a cantilevered heating element and/or cantilevered temperature sensor elements of the measurement structure span a free inner area, for example, the continuous recess or a hole of the gas sensor surrounded by the frame and wherein the gas inlet opening of the pressure sensor or the pressure-sensitive surface, such as a membrane of the pressure sensor borders on the free inner area of the barometric pressure sensor, such that, for example, the distance between pressure measurement membrane and active areas of the measurement structure is smaller than three times the length of one of the active areas or smaller than five times or smaller than the greatest dimension of the free inner area, for example, diagonal or diameter.

This embodiment is based on the knowledge that it is advantageous to use a frame for performing gas measurement of the gas sensor spatially as close as possible to the pressure measurement which is enabled by the frame, and wherein the frame at the same time mechanically supports the gas sensor. At the same time, the frame can seal the gas measurement space (the cavern) to the outside, so that the needed diffusion time up to the complete compensation after change of gas concentration is minimized. Above that, it is advantageous that pressure measurement, for example by a pressure measurement membrane, takes place at a distance from the active area of the gas measurement structure that is smaller than five times or three times the length of active areas or smaller than the greatest dimension of the free inner area, which ensures that the respective measurements practically take place at the same location, which contributes to the elimination of systematic measurement errors.

In a twelfth embodiment, the thermal gas sensor, for example, the carrier material or the frame is connected to the barometric pressure sensor by means of an adhesive, such that the adhesive is not in contact with the gas inlet opening or the pressure-sensitive surface of the barometric pressure sensor. This feature is based on the knowledge that it is advantageous to adhere the thermal gas sensor onto the pressure sensor, since this represents a minimum mechanical additional load for the pressure sensor and hence the pressure sensor is affected as little as possible in its function, in particular when it is ensured that the adhesive is not in contact with the inlet opening or the sensitive surface of the pressure sensor.

In a thirteenth embodiment, the sensor arrangement comprises a printed circuit board material, such as FR4, flex or ceramic, and the pressure sensor and the thermal sensor on top of the same are arranged on one side of the printed circuit board material, or, for example, a printed circuit board, and wherein on the other side of the printed circuit board material facing away from the pressure sensor and the thermal sensor or, for example, the printed circuit board, a plug or a soldering contact for electric contacting is arranged, or wherein the pressure sensor and the thermal sensor on the same are arranged in a recess of the printed circuit board material or, for example, the printed circuit board and wherein on the other side of the printed circuit board material facing away from the pressure sensor and the thermal sensor or, for example, the printed circuit board, a plug or a soldering contact for electric contacting is arranged, and wherein on one side of the printed circuit board material a plug for electric contacting is arranged, wherein, for example, a boundary of the recess of the printed circuit board material limits a gas space of the sensor arrangement.

This embodiment is based on the knowledge that it is advantageous to deposit the sensor arrangement on a printed circuit board material since this allows simplified handling of the sensor arrangement, in particular when a plug or soldering contact can be arranged for simplifying the contacting.

In a fourteenth embodiment, the barometric pressure sensor is a microelectromechanical, MEMS, pressure sensor which can, for example, be a barometric altimeter.

This embodiment is based on the knowledge that it is advantageous to implement the pressure sensor as a microelectromechanical device since this allows a structure that is as compact as possible. Further, it is advantageous that such an MEMS pressure sensor has little weight since it is advantageous to use, in a measurement close to the patient, a sensor arrangement having as little weight as possible in order to minimize the burden on the patient.

In a 15$^{th}$ embodiment, the sensor arrangement includes evaluation means that are configured to determine a gas concentration, for example of a gas proportion of the gas mixture, such as a $CO_2$ concentration, based on phase and amplitude of sensor signals, for example signals from sensor wires or sensor ridges obtained by using the gas sensor and in dependence on pressure information provided by the pressure sensor and possibly temperature information. The evaluation means may, for example, not be integrated on the printed circuit board itself but can be separate from the same but after a respective miniaturization, the same can, for example, be integrated on the rear of the printed circuit board.

This embodiment is based on the knowledge that it is advantageous to determine the gas concentration based on phase and amplitude of sensor signals since this allows a very fast determination of the gas concentration, for example already after a single period of the periodic sensor signal and allows repeated measurement of the gas concentration when several periods of the sensor signals are considered, whereby a series of measurement values is obtained across which averaging can be performed to obtain a statistically more relevant measurement value.

In a $16^{th}$ embodiment, the sensor arrangement is surrounded by a housing providing a volume within the same where the sensor arrangement resides, wherein the housing comprises a housing opening, for example a single housing opening through which a gas to be analyzed can reach the sensor arrangement within the volume from the outside of the housing by a diffusion process, whereby, for example, the housing opening, the measurement structure and the gas inlet opening of the barometric pressure sensor or its pressure-sensitive surface are arranged immediately adjacent.

This embodiment is based on the knowledge that it is advantageous to surround the sensor arrangement by a housing gas-tight to the environment into which the gas to be analyzed can reach by a diffusion process, since the diffusion process represents a steadied gas contrary to a flow process where the gas includes a flow direction and velocity in addition to the molecular movement. A measurement in a flowing medium is more erroneous than the measurement in a diffusing medium since a flowing medium causes transport processes due to the flow, in particular heat transport processes due to the flow which would affect the measurement of the gas concentration.

In a $17^{th}$ embodiment, the opening of the housing comprises a grid that serves as mechanical protection for the sensor arrangement and, for example, optionally as support grid for a membrane.

This embodiment is based on the consideration that a grid in or in front of the housing opening can prevent microscopic particles, for example liquid drops, in the exhaled air from reaching the sensor arrangement, which would affect the function of the sensor arrangement. A further advantage is that such a grid can support a membrane, such a membrane would also be arranged in front of the opening of the housing to also stop particles that cannot be kept away from the sensor arrangement by a grid alone. The usage of a membrane allows, for example, to keep away bacteria and/or viruses from the sensor arrangement, such that the same can be kept sterile.

In an $18^{th}$ embodiment, the opening of the housing comprises a membrane which protects the sensor arrangement from contamination, for example, by humidity, viruses or bacteria and allows diffusion of a gas to be analyzed.

This embodiment is based on the knowledge that the usage of a membrane is advantageous to protect the sensor arrangement from contamination, i.e., to keep the same sterile, which is essential in a clinical environment in order to use the sensor arrangement repeatedly without having to clean or sterilize the same.

In a $19^{th}$ embodiment, the housing comprises an opening, this can, for example, be the only one of the housing through which the gas can reach the inside of the housing, for example in a ready to use state of the sensor arrangement. For example, this provides an area with steady flow in the housing in which the gas sensor resides, such that no flow through the housing takes place and only gas passes through the gas-permeable measurement structure, for example through the level where the wires are arranged, which moves into the pressure chamber that can be a bag measurement chamber of the barometric pressure sensor, for example diffuses into the same or which moves out of the pressure measure chamber of the pressure sensor, for example by diffusion.

This embodiment is based on the knowledge that it is advantageous to provide a steady-flow area containing the thermal gas sensor, since flow through the housing containing the sensor could have an adverse effect on the measurement accuracy of the sensor arrangement since, on the one hand, the gas sensor can be affected in its function by heat transport processes and also the pressure sensor would measure a wrong pressure, usually too small a pressure.

According to a $20^{th}$ embodiment of the present invention, a sensor apparatus includes a flow channel which can, for example, be a hollow cylinder, for example, a flow tube, wherein the flow channel comprises an opening in a wall and includes a sensor arrangement according to one of the embodiments 1 to 17, wherein the sensor arrangement is spatially connected to the inside of the flow channel through the opening in order to allow gas exchange, for example by diffusion between the inside of the flow channel and the sensor arrangement.

This embodiment is based on the knowledge that it is advantageous to combine a flow channel with a sensor arrangement, wherein the sensor arrangement is connected to the inside of the flow channel through an opening in the wall of the flow channel in order to perform gas measurement of the gas within the flow channel, since, on the one hand, the measurement does not take place in the main channel with steady flow and the sensor arrangement due to its spatial arrangement as reusable module which can easily be attached to the flow channel. Usually, the flow channels are inexpensive disposable articles, the sensor arrangement, however, is to be used multiple times. By arranging the sensor arrangement outside the flow channel, a simple structural separation is enabled; further, the lateral arrangement of the sensor enables that the same does not directly immerse in the main channel of the flow but only tangentially touches the flowing inhaled or exhaled air. Due to this structure, there is no flow through the sensor or the sensor arrangement, but a flow-free diffusion process of the gas to be measured into the sensor arrangement takes place, whereby the above-described systematic measurement inaccuracies are omitted.

In a $21^{st}$ embodiment, the opening is covered by a membrane which is, for example, filtering bacteria or viruses, wherein, for example, the membrane is supported by a grid structure that is, for example, porous or fine-meshed, which is arranged in an opening of the housing surrounding the sensor arrangement.

This embodiment is based on the knowledge that it is advantageous to cover the opening by a membrane for example so that bacteria or viruses that are outside the sensor arrangement in the flow channel cannot enter the sensor arrangement, such that the sensor remains sterile or aseptic so that the same can be repeatedly used without having to clean or sterilize the sensor. Since the membrane is to be thin enough to allow diffusion of the gas to be analyzed, the membrane has to be sufficiently thin, whereby the same becomes mechanically fragile, thus, it is advantageous to support the membrane by a grid structure to prevent tearing of the membrane.

In a $22^{nd}$ embodiment, the gas to be analyzed inside the sensor apparatus, which flows, for example, through the flow channel, diffuses through the membrane to the sensor arrangement. The embodiment is based on the knowledge that it is advantageous to let the gas to be analyzed diffuse into the sensor arrangement to prevent measurement value corruption due to flow effects.

In a $23^{rd}$ embodiment, the distance between the membrane of the sensor apparatus and a surface of the gas sensor facing the membrane is smaller than half of the greatest dimension of the flow channel perpendicular to the central flow direction of a gas to be analyzed. The central flow direction is examined, for example, at the location of the opening or in the diameter for a round flow channel or in the diagonal for a rectangular cross-section of the flow channel.

This embodiment is based on the knowledge that it is advantageous to position the gas sensor as close as possible to the membrane, wherein the distance between membrane and sensor is the smaller, the smaller the diameter of the flow channel, i.e., the distance scales with the diameter of the flow channel. If the distance between membrane and gas sensor is as small as possible, the gas sensor can perform the measurement as precise and timely as possible, which results in a measurement which is as accurate and uncorrupted as possible.

In a $24^{th}$ embodiment, the volume surrounding the sensor arrangement which is limited in the direction of the flow channel by the opening, for example by a membrane, for example, the area of a sensor arrangement lying behind the membrane, seen from the flow channel, is less than 1000, 500 or 250 mm$^3$.

The embodiment is based on the knowledge that is it advantageous to limit the volume surrounding the sensor arrangement to a volume that is as small as possible in order to allow an almost complete diffusion of the gas to be measured into the volume in the shortest possible time. Diffusion as fast as possible is desirable since the measurement principle can be based on a phase measurement of a periodic signal and the period of the signal has to be greater than the apparatus-specific diffusion time in order to minimize an adverse effect on the time curve of the measurement value caused by the sensor geometry. At the same time, the frame can seal the gas measurement space (the cavern) to the outside, such that the diffusion time needed up to the complete compensation after a change of gas concentration is minimized.

In a $25^{th}$ embodiment, the sensor apparatus is configured such that the time period up to the compensation of the gas concentration in the area of the gas sensor deviating by at most 0.5 vol % from the gas concentration in the flow channel is less than 10 ms. This can be obtained, for example, by a suitable selection of membrane and gas volume in the chamber behind the membrane containing the sensor arrangement.

This embodiment is based on the knowledge that it is advantageous to keep the time period of the gas concentration compensation as short as possible in order to be able to perform the measurement of the gas concentration in the shortest possible time. It is advantageous that the time is as short as possible since the gas concentration measurement can be based on the measurement of a periodic time signal and when the period of the time signal is in the order of the time period that is needed to compensate the gas concentration, such a measurement cannot be performed without any errors.

In a $26^{th}$ embodiment, the chamber including the sensor arrangement represents an area with steadied flow. This can, for example, be obtained by a suitable arrangement of the opening and/or the geometry of the chamber containing the sensor arrangement and/or by the selection of a membrane or filter structure arranged between the flow channel and the chamber. The chamber can be coupled to the flow channel, for example, by the opening and optionally by a membrane. The region with steadied flow can, for example, be a steadied zone or an almost flow-free zone such that, for example, the gas-permeable measurement structure does not lie in a flow area.

This embodiment is based on the knowledge that it is advantageous to arrange the sensor arrangement in a region with steadied flow since flow effects can have a negative influence on the measurement accuracy of the sensor arrangement since, on the one hand, flows affect the mode of operation of the temperature gas sensor and can also corrupt the pressure measurement.

In a $27^{th}$ embodiment, the sensor apparatus comprises a flow sensor which can determine a flow velocity and/or a gas mass flow and/or volume flow in the flow channel, for example the same can be configured as sensor finger projecting into the flow channel, This embodiment is based on the knowledge that it is advantageous to provide a flow sensor in the sensor apparatus since the same can detect measurement parameters allowing a statement whether the gas sensor is meaningful under the measured conditions, such as flow velocity. Thus, for example in the case of a very large flow velocity, the freedom of flow might not be guaranteed within the sensor arrangement, which could corrupt the measurement values. In this case, potentially corrupted measurement values could be discarded when the flow sensor determines a flow velocity which is above a specific limit.

In a $28^{th}$ embodiment, the sensor apparatus comprises a second barometric pressure sensor measuring an environmental pressure. The sensor apparatus is, for example, configured to determine that breath pressure in dependence on a difference between the pressure values of the first and second pressure sensors.

This embodiment is based on the knowledge that it is advantageous to measure the breath pressure by using the pressure value of the barometric pressure sensor and the second barometric pressure sensor in order to be able to judge whether the gas proportion measurement performed by the sensor arrangement provides a valid measurement result. In the case that the breath pressure lies outside a specific range, the gas measurement might possibly not be accurate.

In a $29^{th}$ embodiment, the sensor apparatus detects a time for calibration based on information on the flow velocity in the flow channel and/or on information on a flow direction in a flow channel, e.g., when it is detected that sufficient fresh air or fresh air enriched with anesthetic gas has been sucked in or applied in order to perform calibration, for example recalibration of the thermal gas sensor, in response thereto.

This embodiment is based on the knowledge that it is advantageous to calibrate or recalibrate the sensor apparatus when needed and that information on the flow velocity or the flow direction in the flow channel are good criteria for deciding whether such a calibration is to be performed.

In a 30th embodiment, the sensor apparatus issues a warning at the time of calibration according to detecting a concentration of a specific gas proportion that is too high, for example higher than a threshold.

This embodiment is based on the knowledge that it is advantageous to issue a warning when a gas proportion that is too high is determined at the time of calibration, so that it can be detected that the calibration has possibly not been performed accurately and the calibration might be performed again, possibly under specific circumstances, for example after flushing the sensor apparatus with a specific gas mixture.

According to a 31st embodiment, a method for producing a sensor arrangement is provided, wherein the method includes providing a barometric pressure sensor and a thermal gas sensor as well as fixing the thermal gas sensor, for example by adhering on the barometric pressure sensor or beside the barometric pressure sensor such that a gas-permeable measurement structure of the thermal gas sensor is arranged, for example directly in front of a gas inlet opening of the barometric pressure sensor or in front of a pressure-sensitive surface, for example a membrane, of the barometric pressure sensor.

According to a 32nd embodiment, a method for operating a sensor apparatus is provided, wherein the method comprises detecting a time for calibration based on information on a flow signal and/or on a flow direction in the flow channel when it is detected, for example, that sufficient fresh air or fresh air enriched with anesthetic gas has been sucked in and performing calibration, for example recalibration, of a thermal gas sensor, for example in response to the detection of a time for calibration.

BRIEF DESCRIPTION OF THE DRAWINGS

Embodiments of the present invention will be detailed subsequently referring to the appended drawings, in which:

FIG. 25 shows a further embodiment with regard to an inventive system architecture;

FIG. 26 shows a further embodiment with regard to an inventive system architecture;

As described above, it is needed for specific applications to determine a $CO_2$ content of gases or gas mixtures. FIG. 1 shows a possible embodiment of a sensor arrangement that is suitable to measure characteristics of gases. The sensor arrangement includes a barometric pressure sensor 10 and a thermal gas sensor 20. The thermal gas sensor is arranged on or beside the barometric pressure sensor 10 and comprises a gas-permeable measurement structure 22 which can, for example, be a hole, wherein the measurement structure is arranged such that the same is in front of the pressure-sensitive surface or the gas inlet opening of the pressure sensor. Due to the fact that the pressure sensor is in immediate proximity to the gas sensor, it can be ensured that both the pressure measurement and the measurement of the gas essentially take place at the same location. This is advantageous since the measurement values of the thermal gas sensor 20 can be different, depending on what pressure and what temperature prevail in the area of the thermal gas sensor. If, for example, the pressure and temperature dependency of the measurement values of the thermal gas sensor 20 is known, the same can possibly be adapted or interpreted accordingly. This contributes to increasing the significance of the measurement values of the thermal gas sensor 20.

Such an arrangement 100 represents a miniaturized sensor system that serves to determine the concentration of gases or gas mixtures, for example to determine a $CO_2$ concentration in expiration gas during exhalation close to the patient, which can be implemented as a so-called chip scale package. Such a chip scale package is generally a housing in the order of an electronic chip and in this case includes a pressure sensor as well as a gas sensor. This sensor arrangement 100 can further include a gas-tight measurement chamber and can be connected to a flow channel through which, for example, the breathing gas of a patient is guided, for example, via a lateral bore of such a channel.

Figure 1:
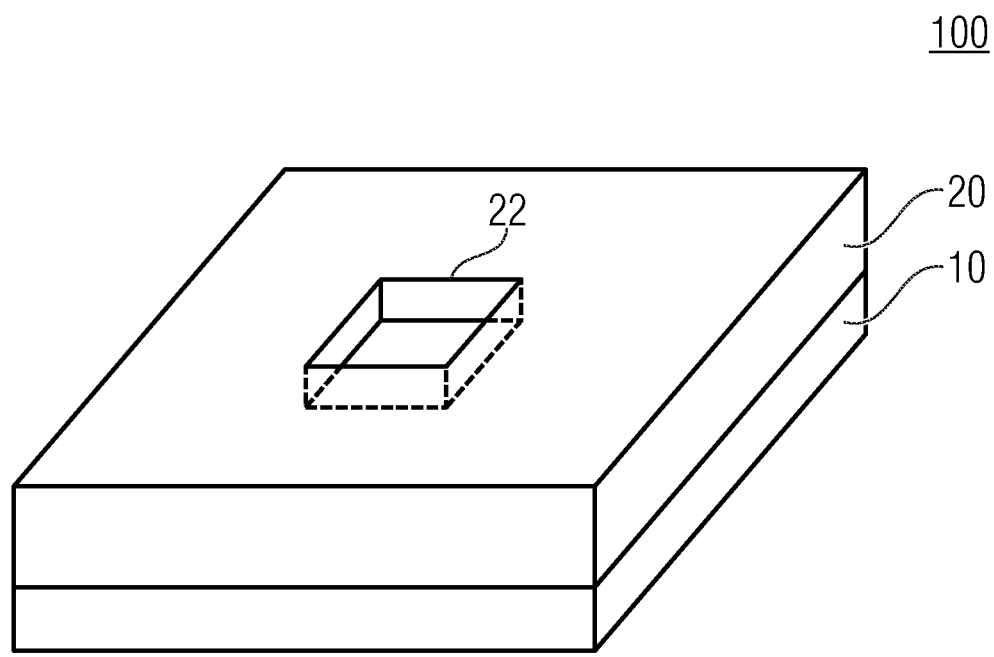
FIG. 1 shows a schematic illustration of a sensor arrangement according to an embodiment.

Although the sensor arrangement 100 is shown in FIG. 1 in a square configuration, it is obvious that the same can be configured in a rectangular, round or also polygonal manner. The same applies for the permeable measurement structure 22 shown in a square manner in FIG. 1. It is also obvious that this measurement structure can also be rectangular, polygonal, round or also oval or can also be irregularly formed.

Figure 2:
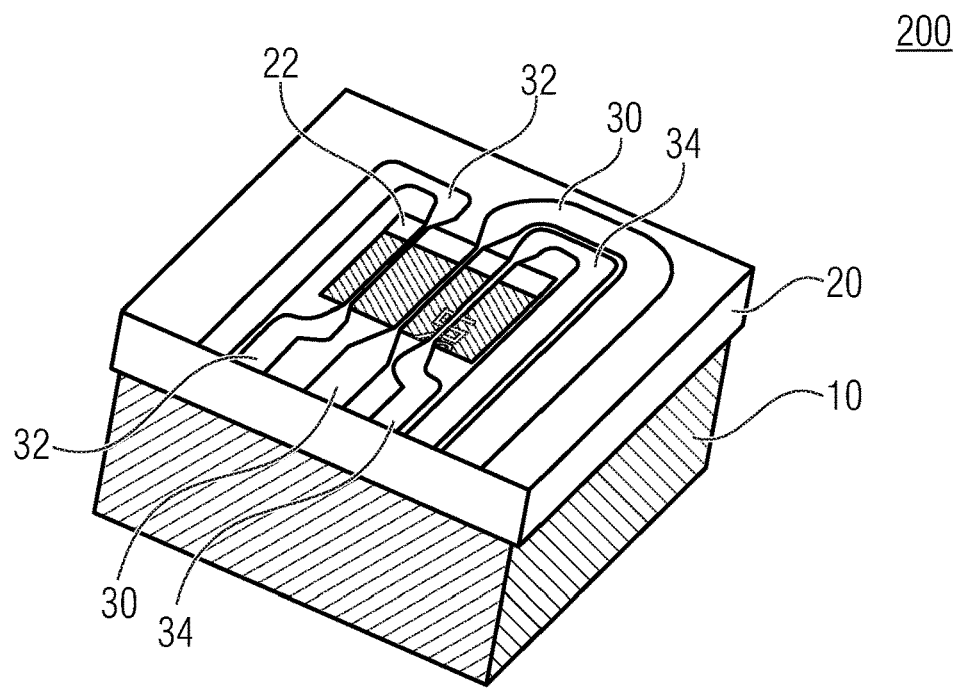
FIG. 2 shows a further embodiment of the sensor arrangement as already described in the context of FIG. 1.

FIG. 2 shows a further embodiment of the sensor arrangement as already described in the context of FIG. 1. The sensor arrangement 200 comprises a barometric pressor sensor 10 and a thermal gas sensor 20. In this embodiment, the thermal gas sensor includes three electric conductor structures 30, 32 and 34. The conductor structures span the area of the permeable measurement structure 22. The part of the conductor structures 30, 32, 34 spanning the gas-permeable measurement structure 22 can be configured as wire or ridge. In one embodiment, the central wire 30 is configured to be provided with a heating signal, the wires 32 and 34 arranged on both sides of the central wire are arranged at different distances to the central wire 30 and serve as temperature sensors. The mentioned wires can, for example, be crystalline silicon wires.

In this example, the thermal gas sensor shown in FIG. 2 includes three cantilevered filigree crystalline silicon wires surrounded by the gas to be analyzed. The wires can be spanned between a frame supporting the same. The central wire can be provided with a heating signal, the same can be a periodic heating signal. The two wires arranged asymmetrically on the left and right relative to the heating wire operate as temperature sensors. These temperature sensors measure the heat transfer from the heating wire to the sensor wires, the heat transfer takes place via the usually unknown heat transmissions from the heating wire into the gas to be analyzed and from this gas to the sensor wires. By measuring the temperature response with two sensor wires that are generally identical but are arranged at different distances to the heating wire, the unknown heat transmissions in the measurement arrangement can be eliminated. By measuring phase and amplitude of the two sensor signals in the two sensor wires, components of the gas or gas mixture can be inferred, the phase and amplitude essentially depend on the heat transfer through the gas.

Figure 3:
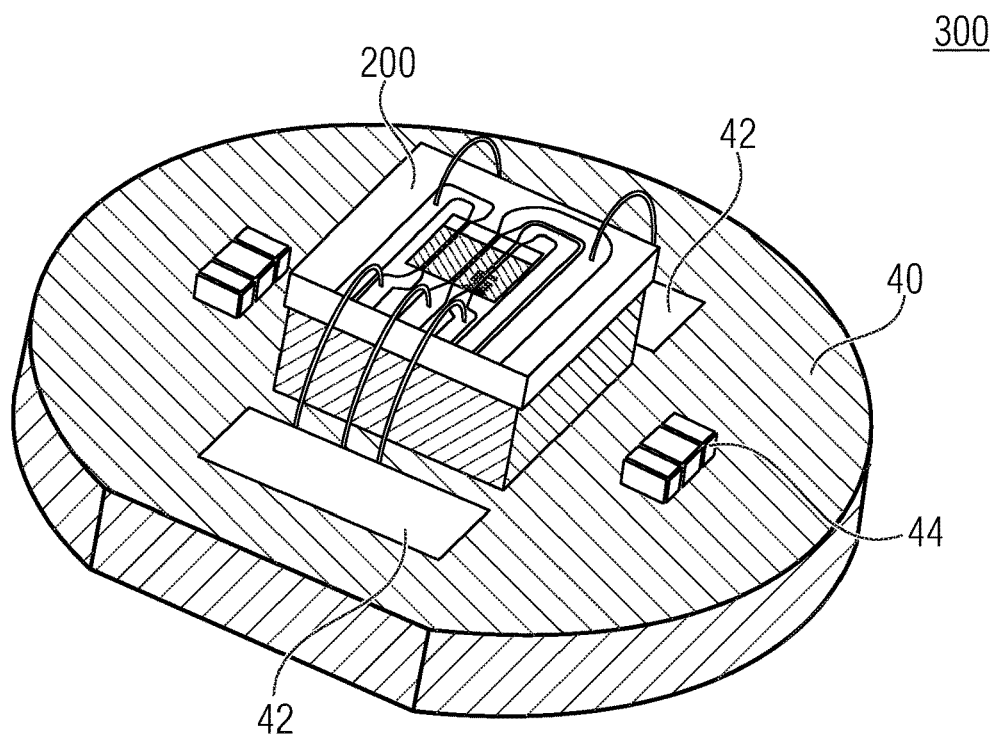
FIG. 3 shows a sensor system configured as chip scale package.

As mentioned above, the sensor system can be configured as chip scale package and includes in this case, as shown in FIG. 3, a printed circuit board 40, a barometric pressure sensor 10 which can be a microelectromechanical (MEMS) pressure sensor with, for example, 24 Bit resolution such as a barometric altimeter and includes a thermal sensor 20 adhered over the same which can also be a microelectromechanical member.

For contacting the sensor system 200, the round printed circuit board comprises contacting apparatuses 42 allowing contacting of the electric conductor structures of the sensor arrangement 200 by means of bonding wires. Further, the printed circuit board can include electric members such as capacitors, diodes or active electronic members 44 being used, for example, during operation of the sensor system. Entire miniaturized evaluation circuits can be arranged on the module.

Figure 4:
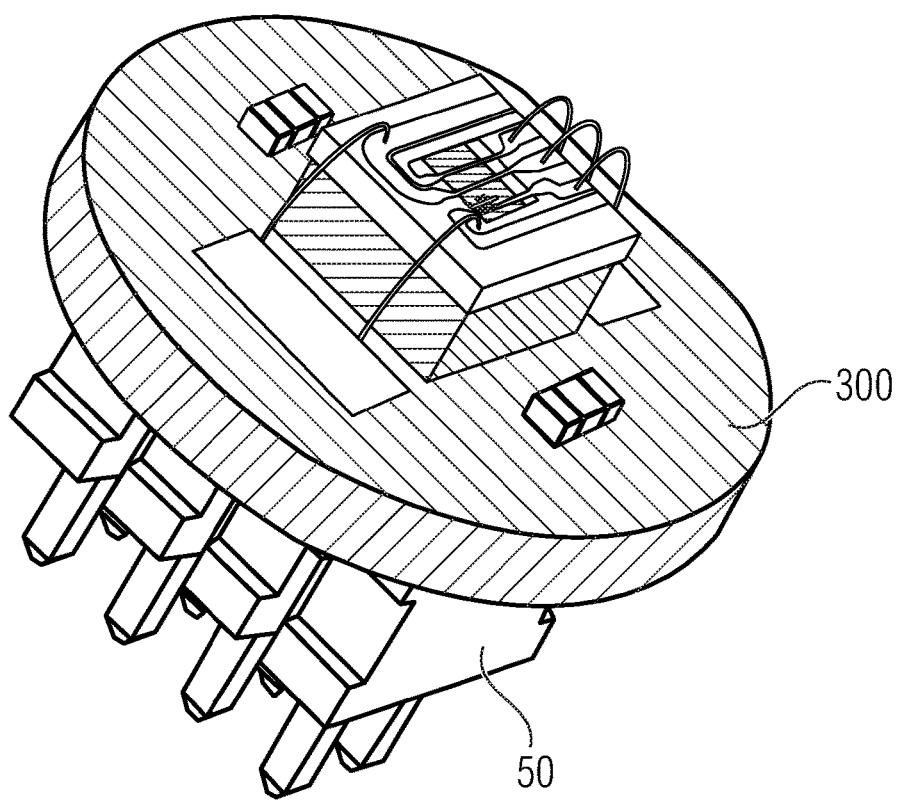
FIG. 4 shows a plug for electric contacting arranged on the rear of the printed circuit board.
Figure 6:
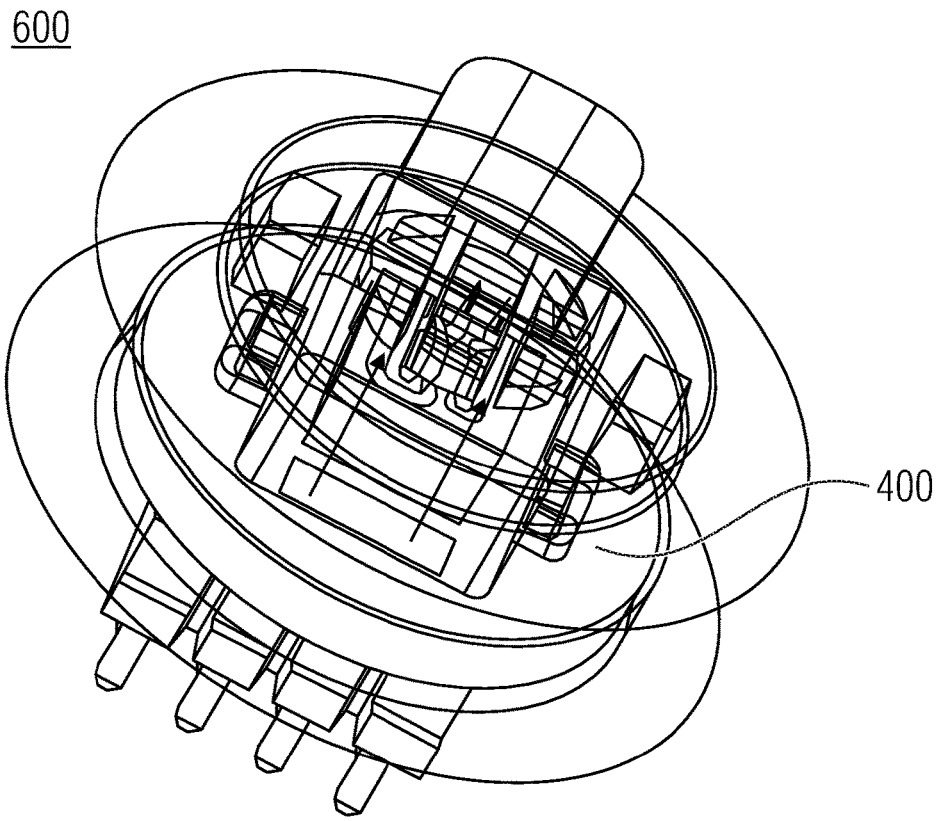
FIG. 6 shows the sensor arrangement with printed circuit board and plug on the rear which enclosed by a housing.

As shown in FIG. 4, a plug for electric contacting can be arranged on the rear of the printed circuit board 40. This plug which can, for example, be a fine pitch plug, a spring contact system or a fixed solder connection allows standardized and easy contacting of the sensor system. The entire sensor system can be enclosed, for example, by a housing as shown in FIG. 6. FIG. 6 shows the sensor arrangement with printed circuit board and plug on the rear which is enclosed by a housing.

Figure 5:
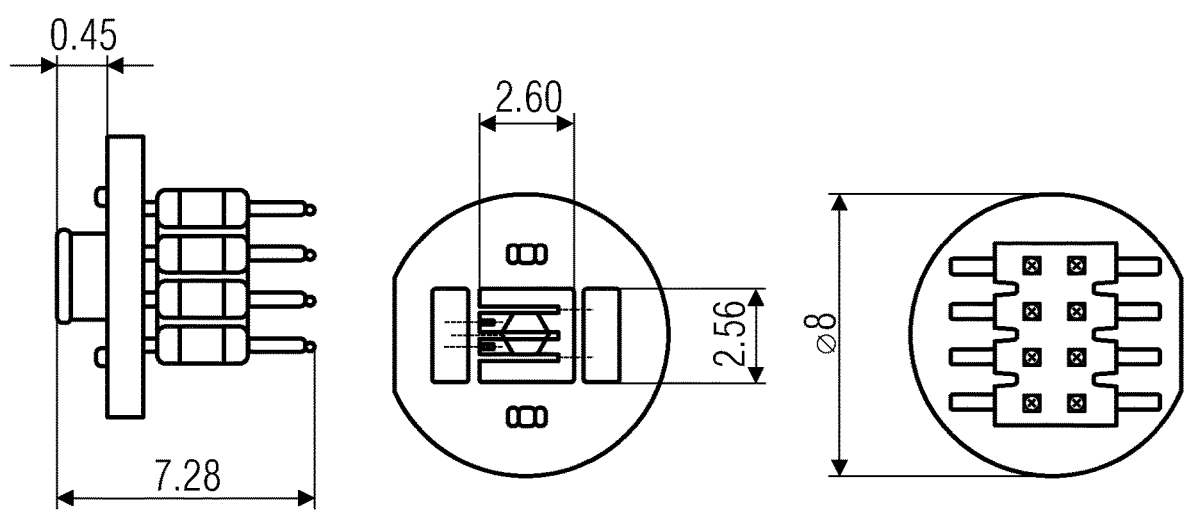
FIG. 5 shows the entire sensor stack as shown in FIG. 4 once in a lateral view, in a top view and a view from the plug side.

FIG. 5 shows the entire sensor stack as shown in FIG. 4 once in a lateral view, in a top view and a view from the plug side. The dimensions are in millimeters whereby it becomes clear that the sensor system has a very small structure. Thus, the diameter of the printed circuit board is 8 mm and the edge dimension of the pressure sensor are at approximately 2.6 mm. This results in a very small structure of, for example, approximately 1 $cm^3$ with regard to the outer dimensions. If the sensor is surrounded by a housing the gas measurement space is, for example, approximately 250 $mm^3$. Here, the sensor arrangement provides the measurement of pressure, temperature and gas concentration, for example $CO_2$ concentration. Measurement of pressure and temperature takes place, for example, in the gas sensor or the so-called $CO_2$ module. This enables a very exact drift correction, for example of a $CO_2$ concentration measurement.

Figure 7:
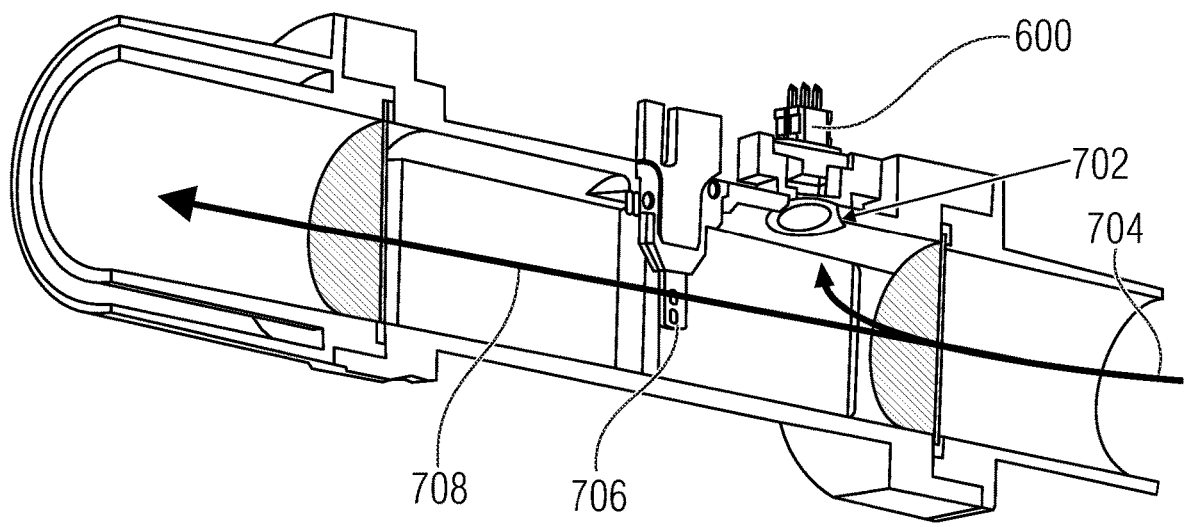
FIG. 7 shows an embodiment of the sensor arrangement with a flow channel 700 configured as disposable respiration tube.

FIG. 7 shows an embodiment of the sensor arrangement with a flow channel 700 configured as disposable respiration tube (flow tube). The shown apparatus serves, for example, to determine a concentration of gases, here to determine the $CO_2$ concentration in the exhaled air of the patient close to the patient. The flow channel 700 has an opening in a wall, wherein the sensor arrangement 100 configured as $CO_2$ module is arranged in a measurement chamber. The sensor arrangement is spatially connected to the inside of the flow channel 700 through the opening in order to allow gas exchange between the inside of the flow channel 700 and the sensor arrangement. A grid structure 702 is arranged at the opening to the flow channel 700, through which the gas exchange takes place. During an inspiration phase of the patient (inspiration 704), fresh air or a calibration gas passes along the $CO_2$ module in the measurement chamber. During an expiration phase of the patient, exhaled air passes along the sensor arrangement, wherein the $CO_2$ concentration in the exhaled air of the patient can be measured.

Due to the lateral arrangement of the sensor, the same does not immerse directly into the main channel of the flow but only tangentially contacts the flowing inhaled or exhaled air. Due to this structure, no flow takes place through the sensor or the sensor arrangement, but a flow-free diffusion process of the gas to be measured into the sensor arrangement takes place, whereby systematic measurement inaccuracies are omitted.

The opening to the measurement chamber is covered by a membrane so that bacteria or viruses that might be outside the sensor arrangement in the flow channel 700 cannot get into the sensor arrangement such that the sensor remains sterile or aseptic so that same can be used repeatedly.

Further, the sensor apparatus of FIG. 7 comprises a flow sensor 706 that can determine a flow velocity and/or a gas mass flow 708 and/or a volume flow in the flow channel 700. By this flow sensor 706 configured as sensor finger projecting into the flow channel 700, measurement parameters can be detected that allow a statement on whether the gas sensor is significant under the measured conditions, such as flow velocity. Thus, for example in the case of a very large flow velocity, the flow freedom within the sensor arrangement might not be guaranteed, whereby the measurement values might be corrupted.

In the following, further embodiments and aspects of the invention will be presented. It should be noted that the embodiments can be used separately. Further, the different features, functionalities and details of the individual embodiments can also be used in other embodiments as long unless no compelling technical reasons are opposing this.

One embodiment relates to a miniaturized sensor system for determining the concentration of gases, for example for determining the $CO_2$ concentration in the expiration gas during expiration close to the patient which is configured as chip scale package that is connected to the main stream channel with a gas-tight measurement chamber and via a lateral bore.

The chip scale package of FIG. 4 includes, for example, a round printed circuit board, a barometric MEMS (microelectromechanical) pressure sensor (having, for example, 24 bit resolution, barometric altimeter) and, for example, a thermal sensor (MEMS or microelectromechanical, Hahn-Schickard) adhered over the same. A fine pitch plug, a spring contact system or a fixed solder connection for electrical contacting is arranged on the rear. The sensor stack is enclosed, for example, by an RP (rapid prototyping) housing having, for example, a grid structure and a recess for receiving an O-ring ceiling against leaking at its opening to the flow tube.

The advantages of such an arrangement are, for example: A very small structure, for example, 1 $cm^3$ (outer dimensions) with a gas measurement space of, for example, approximately 250 $mm^3$ and providing functionality for a measuring pressure, temperature and $CO_2$ concentration. Measuring pressure and temperature takes place, for example, in the $CO_2$ module (e.g., in the gas sensor), wherein exact drift correction (for example of a $CO_2$ concentration measurement) can be possible. Measuring the airway pressure can, for example, take place by differentiation between the two barometric pressure sensors (in the module and in the device).

Further advantages are, for example:
very small gas measurement chamber,
very fast gas exchange via diffusion through virus filters,
very little breathing gas is needed for analysis, small dead space volume,
instantaneous $CO_2$ concentration is measured directly at the mouth piece in the tracheal tube,
Fast diagnosis of the metabolic state of the patient,
measurement directly at the tube
measurement by bacteria/virus filters,
no time delay: breath-resoluted concentration determination of the $CO_2$ concentration,
Low energy requirements non-consumptive physical measurement principle
Auto calibration at the end of the inspiration phase to fresh air concentration,
Mechanically and fluidically reliable easy and quick to replace apparatus via snap-in noses for clamping the flow tube into the reusable device.

In the following, a further embodiment according to the present invention will be shown and described.

FIG. 7 shows a gas flow during inspiration: flushing the small chamber including the sensor module with fresh air or specific gases (for example, for anesthesia) which can be used as calibration gases. Here, the gas exchange takes place via a virus filter.

Figure 8:
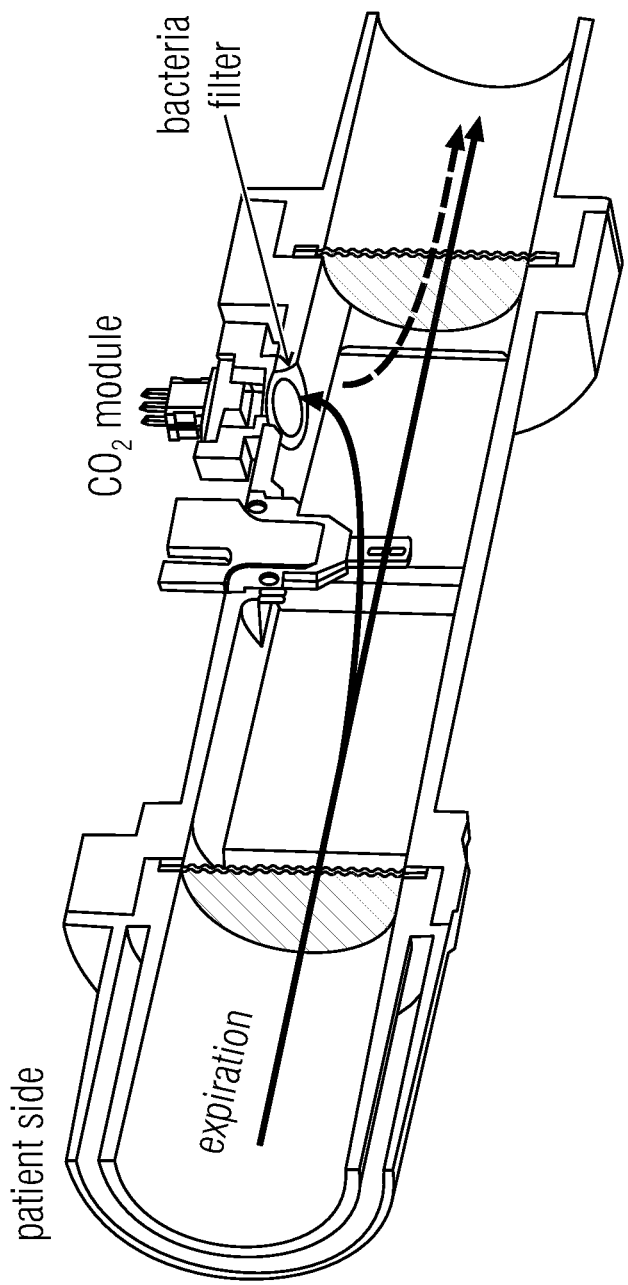
FIG. 8 shows a gas flow during expiration.

FIG. 8 shows a gas flow during expiration: here, the $CO_2$ concentration in the exhaled air of the patient can be evaluated. For the diffusion of the $CO_2$ molecules through the bacteria filter, exemplarily, a diffusion time of 7.2 ms is needed at the sensor for a concentration leap to 5 vol % with 1 μm mesh size.

Characteristics of such an embodiment are, for example:
disposable flow tube with virus filter,
decoupling the measurement gas via diffusion,
leakage-free connection via O-rings and/or area sealing and/or molded 2K plastic seal,
secure apparatus via snap-in noses,
$CO_2$ module is within the reusable device.

The following embodiment shows, for example, a structure of a thermal gas sensor and a respective sensor principle.

Figure 9:
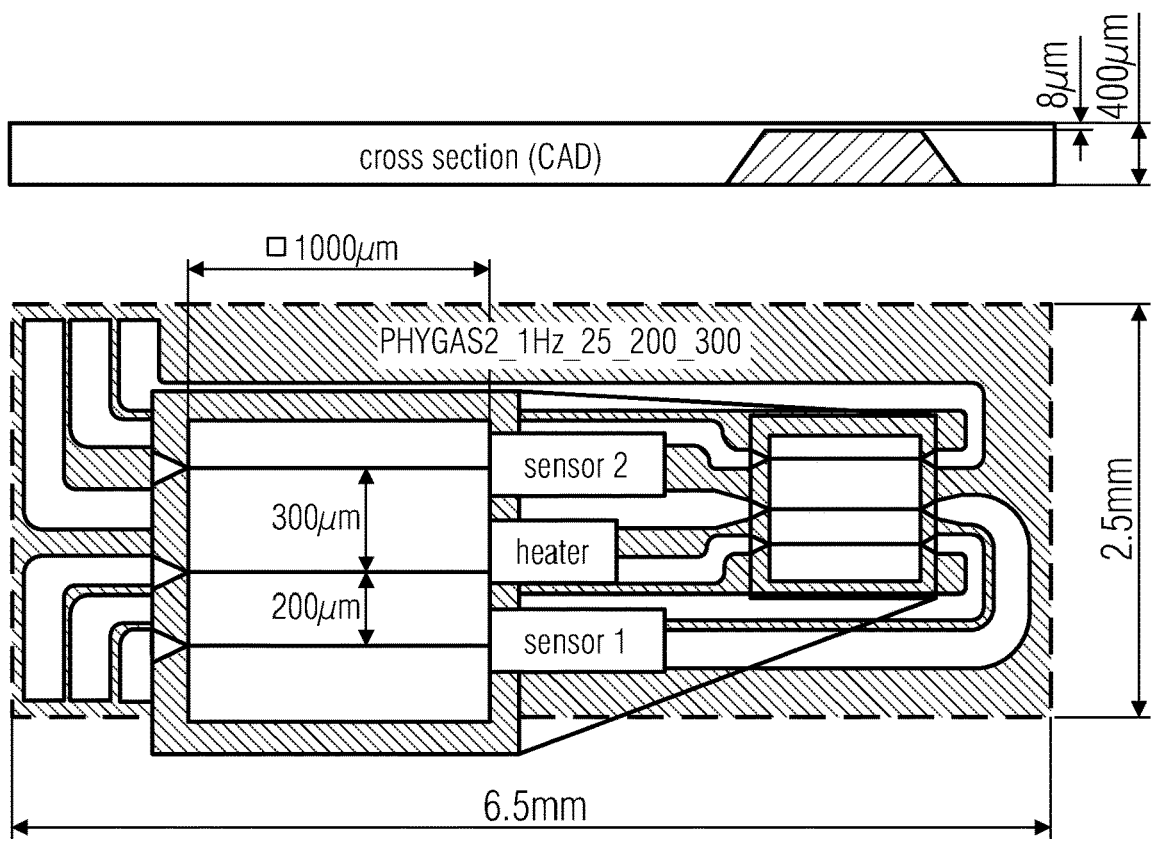
FIG. 9 shows the thermal gas sensor of FIG. 9 consisting of, for example, three filigree crystalline silicon wires cantilevered between a frame surrounded by gas to be analyzed.
Figure 10:
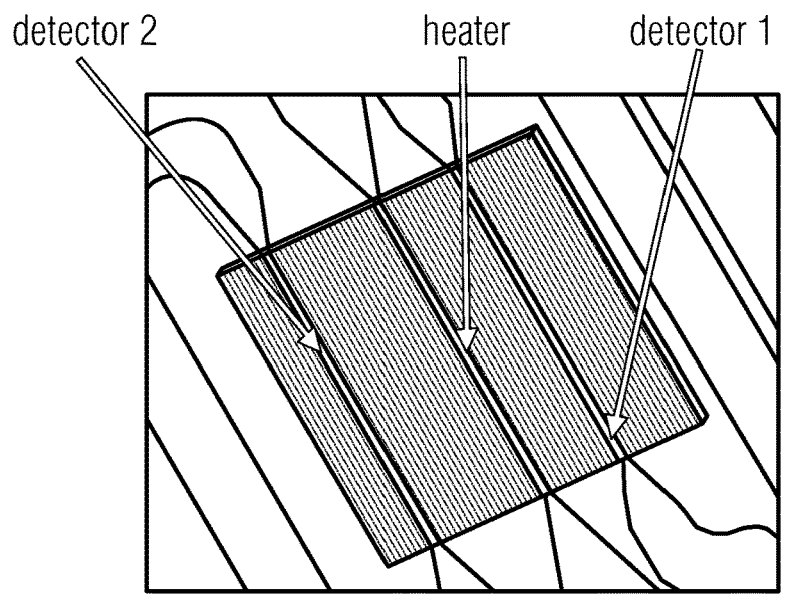
FIG. 10 shows a sensor chip with silicon micro wires for differentiating gas mixtures.

The thermal gas sensor of FIG. 9 and FIG. 10 consists of (or includes), for example, three filigree crystalline silicon wires cantilevered between a frame surrounded by gas to be analyzed. FIG. 10 shows a sensor chip with silicon micro wires for differentiating gas mixtures. The central wire is, for example, provided with a periodic heating signal, the two silicon wires arranged unsymmetrically on the left and right of the heater operate as temperature sensors. Heat transfer takes place via the unknown heat transmissions from the heater into the gas to be analyzed and from the gas into the sensor wire. By measuring the temperature response with two identical sensors at different distances to the heater, the unknown heat transmissions in the measurement arrangement can be eliminated. Phase and amplitude of the two sensor signals essentially depend on the heat transfer through the gas.

Figure 11:
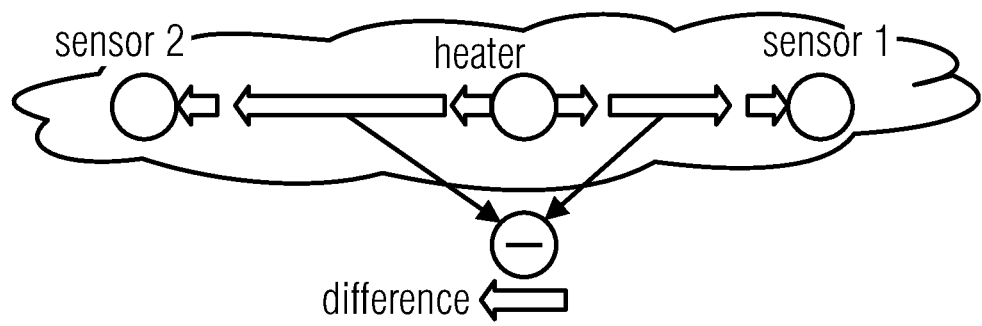
FIG. 11 shows schematically the basic principle of the thermal sensor.

FIG. 11 shows schematically the basic principle of the thermal sensor: The special separation of heater and sensor wires can clearly be seen with thermal coupling by the gas mixture to be analyzed, as well as the measurement with sensor wires at different distances to the heater.

Heater and sensor(s) are separately arranged in the medium and are surrounded by the gas to be analyzed. The heat flow from the heater to the temperature sensors only takes place via the gas itself. The heat transport also takes place via the unknown heat transmissions from the heater to the gas to be analyzed and from the gas into the sensor wire. When measuring at two distances, the heat transmissions are almost the same. The difference of both sensor signals essentially depends on the heat transfer through the medium itself.

Electrical Analogy: For identifying and estimating the heat flows, an electric analogy has been established. Optimizing the heat loss is an essential factor for increasing the sensitivity of the sensor without having to feed too high a heating power.

Figure 12:
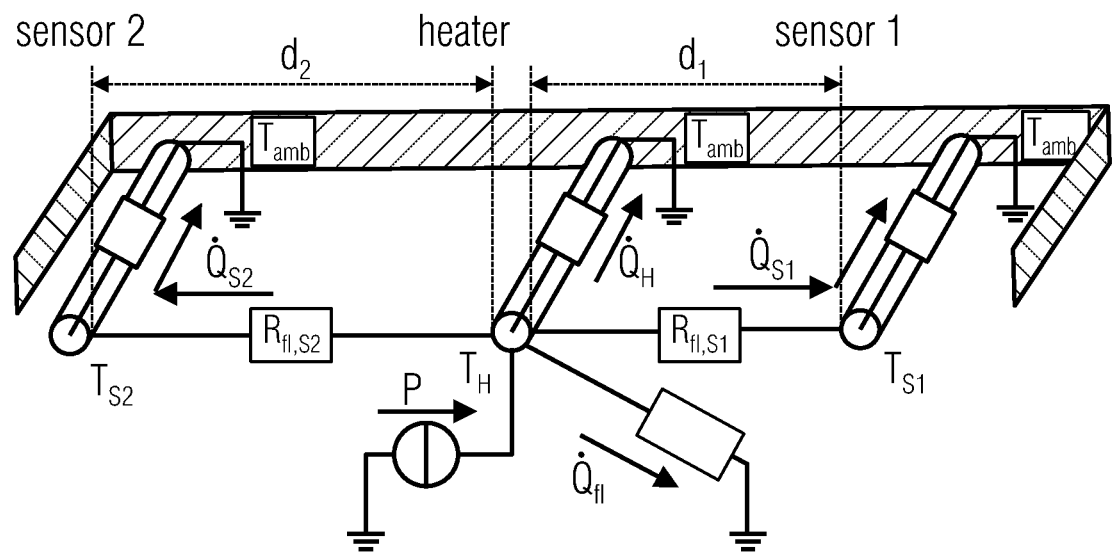
FIG. 12 shows a schematic illustration of the heat transport at the sensor.

FIG. 12 shows a schematic illustration of the heat transport at the sensor. The heat transport from the heater (temperature TH) to the sensor (temperature TS) essentially takes place through the gas to be measured.

For a sinusoidal heating power, a sinusoidal curve of the sensor signal results, which heavily depends on the thermal characteristics of the gas surrounding the sensor wires. By measuring the temperature of the heater with two identical sensors at different distances to the heater, the unknown heat transmissions in the measurement arrangement can be eliminated, as already described above.

Figure 13:
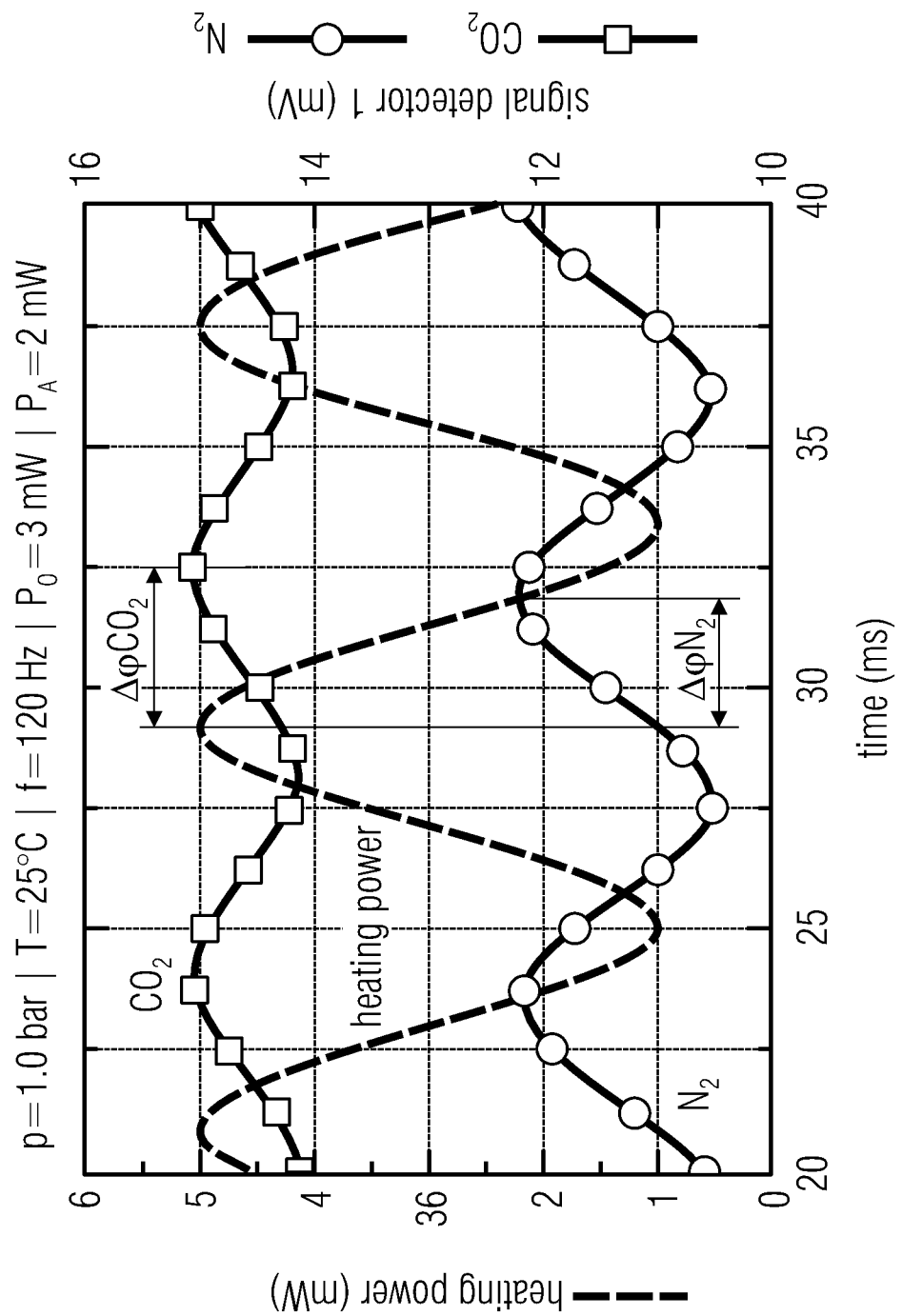
FIG. 13 shows emitted and received sinus waves that are compared for evaluation.

As illustrated in FIG. 13, emitted and received sinus waves are compared for evaluation. With a calibration of the signal via the phase shift between heater and sensor, for example, the $CO_2$ content in air can be resoluted with 0.2 vol %. Since gases can be compressed and change their density due to pressure and temperature, the respective drifts are to be compensated.

By evaluating further measurement parameters provided by the sensor, heat conductivity, temperature conductivity and with a known density of the gas also the specific heat capacity can be determined—a possible way for also analyzing unknown gas mixtures.

FIG. 13 further shows signals when exciting with sinusoidal heating power for $CO_2$ and $N_2$ in comparison. With the same heating power, the received sensor signals differ in amplitude, offset and phase position.

By the structural difference of cantilevered bridge structures with respect to closed thin layer membranes, the parasitic thermal decoupling between heater and detector elements is mostly obtained and the signal quality is significantly increased. Due to the low thermal mass of the heater it is possible to modulate the heater with frequencies of up to 300 Hertz since heat can be quickly supplied and discharged.

Figure 14:
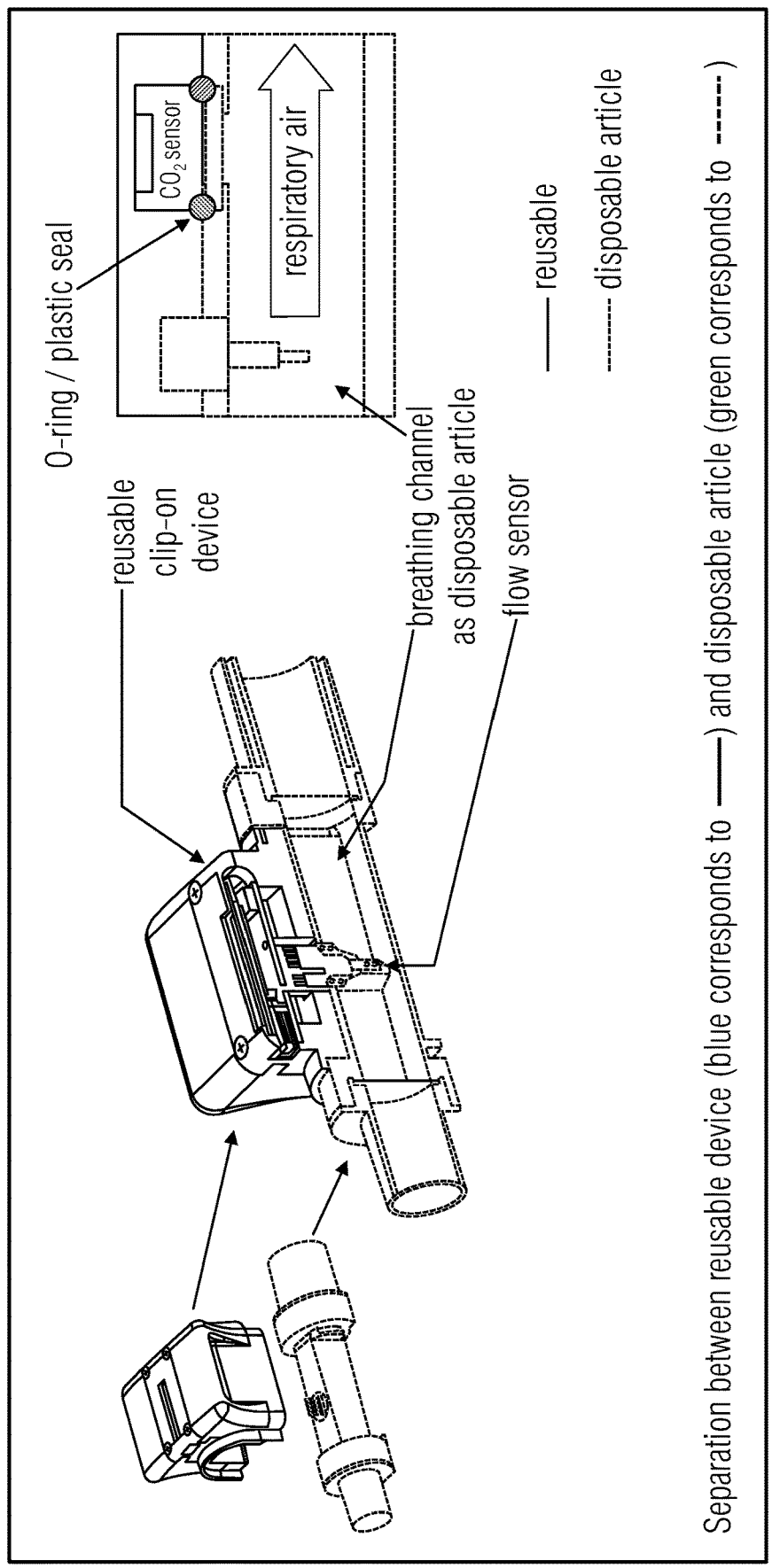
FIG. 14 shows a separation between reusable device and breathing channel as disposable article.

A further aspect of the invention relates to a separation into a reusable device and a breathing channel which can, for example, be a disposable article. FIG. 14 shows such a separation between reusable device and breathing channel as disposable article. In the left image, the breathing channel is illustrated as disposable article green/left shaded. The same consists of a breathing flow channel with standard cone connections and optionally includes an MEMS flow sensor and a filter.

The part illustrated in blue/right shaded is a measurement device that can be clipped onto the breathing channel and can, for example, be reused multiple times since it does not come into contact with the breathing gas of the patient. The light-blue/cross-shaded block in the illustration of the right side of FIG. 14 schematically shows the gas measurement space as cavity in the sensor housing with a size of approximately 250 mm³. The $CO_2$ sensor, for example, a thermal gas sensor, is within this cavity and is protected against touch to the outside by a grid.

The optional virus/bacteria filter prevents that the $CO_2$ sensor is contaminated by the breathing gas of the patient. Here, the filter is a disposable article as a component of the breathing channel. The leakage-free port of the gas measurement chamber of the $CO_2$ sensor is either obtained by O-rings, an area seal or via a molded 2K plastic seal which can either be part of the reusable device or part of the breathing channel.

A further aspect of the invention relates to the estimation of the diffusion time up to a concentration compensation. The $CO_2$ sensor should, since the same belongs to the reusable part, be protected as much as possible from any contamination by the breathing gas of the patient. For that reason, a virus/bacteria filter separates the contaminated area in the breathing channel from the non-contaminated reusable measurement device with the $CO_2$ sensor. The filter is, for example, part of the breathing channel (the disposable article) since the same is contaminated by the breathing gas of the patient.

Figure 15:
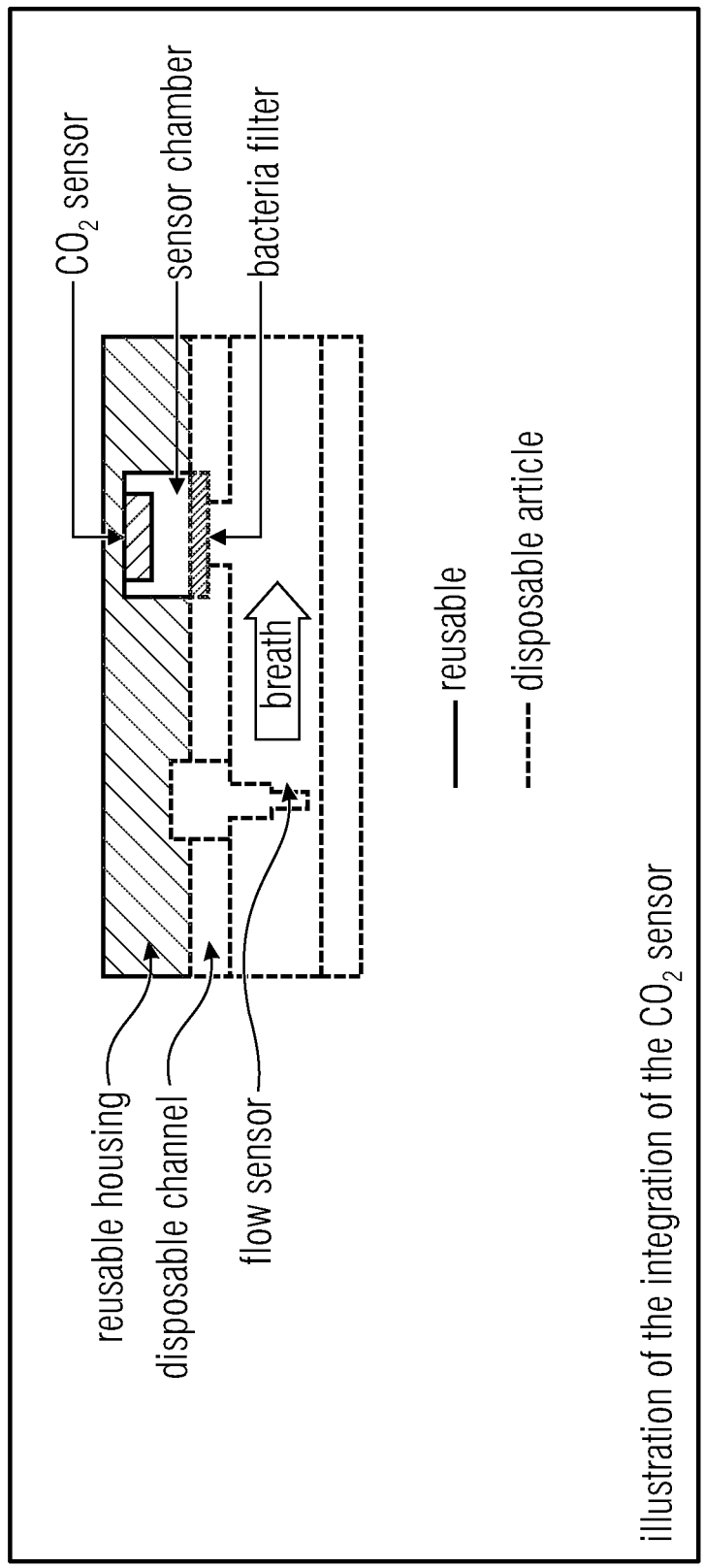
FIG. 15 shows an embodiment of a $CO_2$ sensor.

FIG. 15 shows in a schematic illustration an embodiment of a $CO_2$ sensor. The same comprises:
reusable clipped housing
disposable channel
flow sensor (belongs to disposable channel)
breath
$CO_2$ sensor
sensor chamber
bacteria filter
disposable
reusable The filter reduces the diffusion velocity of the $CO_2$ molecule into the gas measurement chamber of the sensor housing, which increases the response time of the sensor. Therefore, the diffusion time up to the compensation of the concentration in the breathing channel and in the gas measurement chamber of the sensor has to be estimated with respect to filter diameter and pore size.

Figure 16:
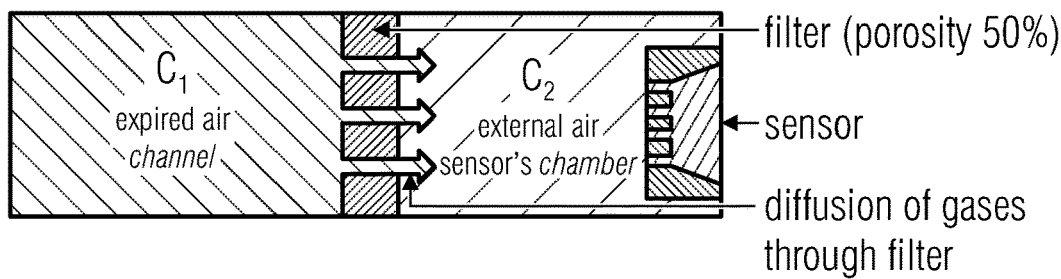
FIG. 16 shows a calculation by simplified static boundary conditions.

FIG. 16 illustrates a calculation by simplified static boundary conditions at a temperature of 300 K, atmospheric pressure and without considering the breath humidity.

The parameters influencing the diffusion according to Fick's law are:
expired air
external air
channel
sensor chamber
filter
porosity
sensor
diffusion of gases through the filter For the diffusion flow J, the first Fick's law defines the following context:

$$J = -D \frac{\partial \varphi}{\partial x}$$

$$J = -D \frac{(C_2 - C_1)}{\delta}$$

wherein D is the diffusion coefficient of gas 1 into gas 2 (assumed to be constant), C1 and C2 are the concentrations of the substance in the two gases and δ is the geometrical relation.

For the calculation, the following parameters have been determined: $CO_2$ concentration of the expiration gas C1=1.62 mol·m⁻³, $CO_2$ concentration in fresh air C2=1.62·10-3 mol·m⁻³, diffusion coefficient D=14·10⁻⁶ m²·s⁻¹ (diffusion coefficient for $CO_2$ in air at atmospheric pressure at 300 K) and for the filter membrane a porosity of 0.5 at a thickness δ=10 μm and an effective membrane area of S=1.03·10⁻⁴ m², wherein the volume of the sensor chamber (the gas measurement space) with V1=5.14823·10⁻⁷ m³ at a first prototype and with V2=1.378·10–7 m³ at the current sensor structure has been assumed. This results in a diffusion flow of J=2.25 mol·m-2·s-1, which means that an amount of substance of 2.25 Mol $CO_2$ would pass through a filter area of 1 m² per second. Converted to the actual filter area, a flow of a few μmol/s results that is sufficient to bring the gas measurement chamber to the concentration C1 of the expiration gas after 7.2 ms (first prototype).

Figure 17:
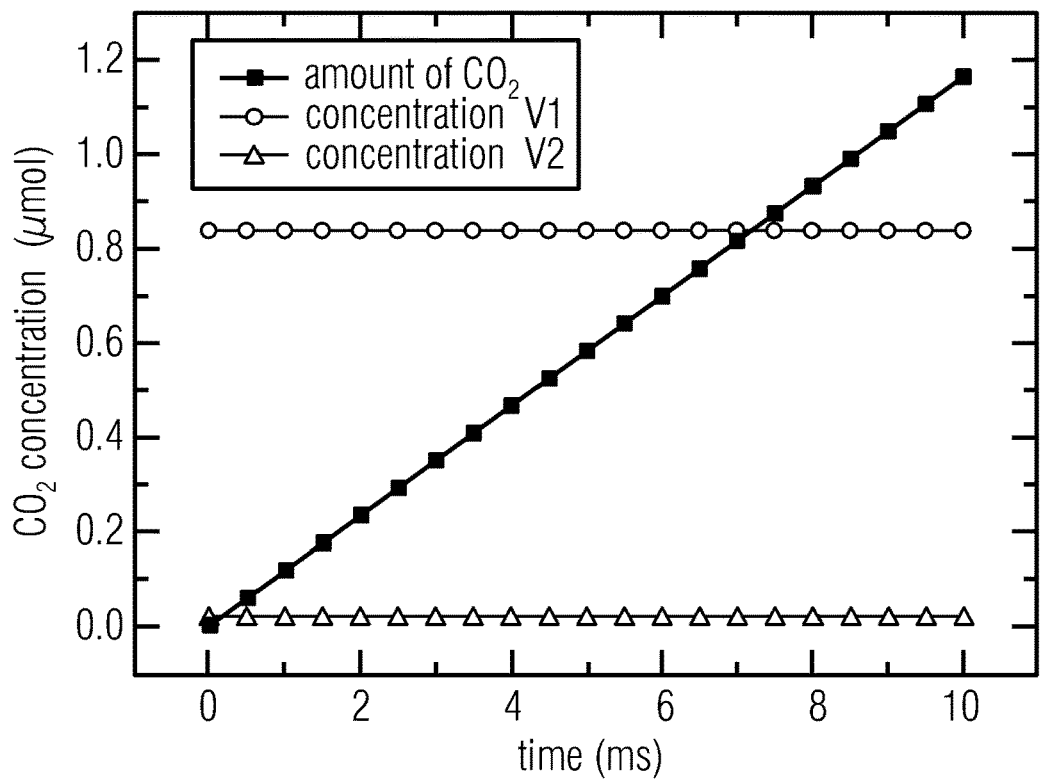
FIG. 17 shows a temporal diffusion curve.

If the gas measurement chamber with V2 is by a factor 30 smaller than V1, this results in a delay time up to the concentration compensation of only approximately 0.2 ms. The temporal diffusion curve in FIG. 17 shows that the smaller the gas measurement chamber is selected the faster the concentration compensation at the sensor takes place.

The result of the estimation is underdetermined since the actual diffusion time up to the concentration compensation shortens further due to the pressure increase during expiration in the breathing channel according to the Wrobleski equation:

$$J = P \frac{(p_2 - p_1)}{\partial x}$$

wherein p1 is the pressure in the breathing channel, p2 is the pressure in the gas measurement chamber and P is the permeability of the filter. At a gas flow in the channel, the difference p2–p1 increases, such that the diffusion flow increases and the $CO_2$ diffusion through the filter also increases. This pressure difference results in a flow into the sensor chamber which supports the gas diffusion through the filter.

Influence of the flow on the sensor signal: The signal of the $CO_2$ sensor can easily be disturbed since it shows a lower sensitivity compared to the thermal flow signal. Thus, the parasitic influence of the flow on the signal of the $CO_2$ sensor should be prevented in order to be able to accurately measure the gas concentration.

In one embodiment, filter, geometry of the inflow grid and miniaturized gas measurement chamber provide a steadied area where the thermal sensor can operate undisturbed from the outer flow.

Possible fields of application of the embodiments of the invention are, for example, in medical technology for respiration of patients (capnometry) or in natural gas analysis where, for example, the fuel value of a gas is to be determined. For capnometry, different $CO_2$ sensors are used which are summarized below. The absorption at the $CO_2$ molecules is mainly measured by infrared spectroscopy.

Figure 18:
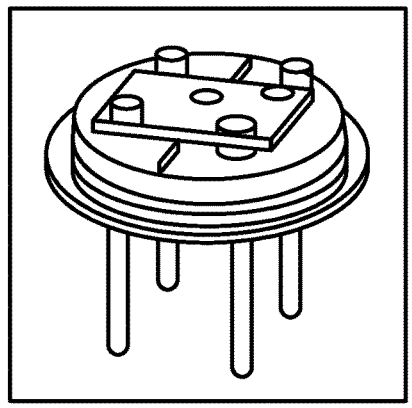
FIG. 18 shows an embodiment of a metal oxide sensor (MOX)

FIG. 18 shows an embodiment of a metal oxide sensor (MOX).

Figure 19:
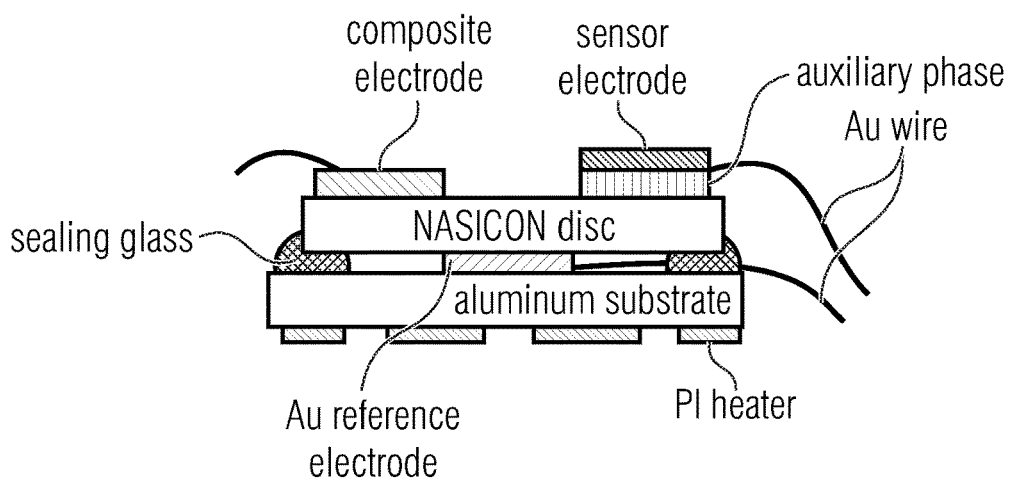
FIG. 19 shows an embodiment of an electrochemical potentiometric sensor (NASICON)

The advantages of the same are:
simple principle (chemical reaction of a thin layer)
sensitivity at small concentrations
cost-effective The disadvantages of the same are:
sensor is consumed
no long-time stability
low selectivity of the gas type
not suitable for $CO_2$
operating temperature up to 800° C. and accordingly risk for the usage in the main stream FIG. 19 shows an embodiment of an electrochemical potentiometric sensor (NASICON).

The advantages of the same are:
high accuracy
small dimensions

Figure 20:
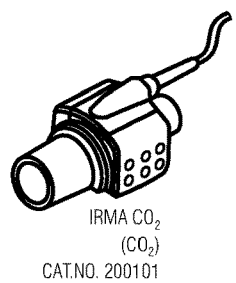
FIG. 20 shows an embodiment of a non-dispersive infrared sensor (NDIR)

The disadvantages of the same are:
electrode material is consumed
relatively expensive for a short life span FIG. 20 shows an embodiment of a non-dispersive infrared sensor (NDIR).

Figure 21:
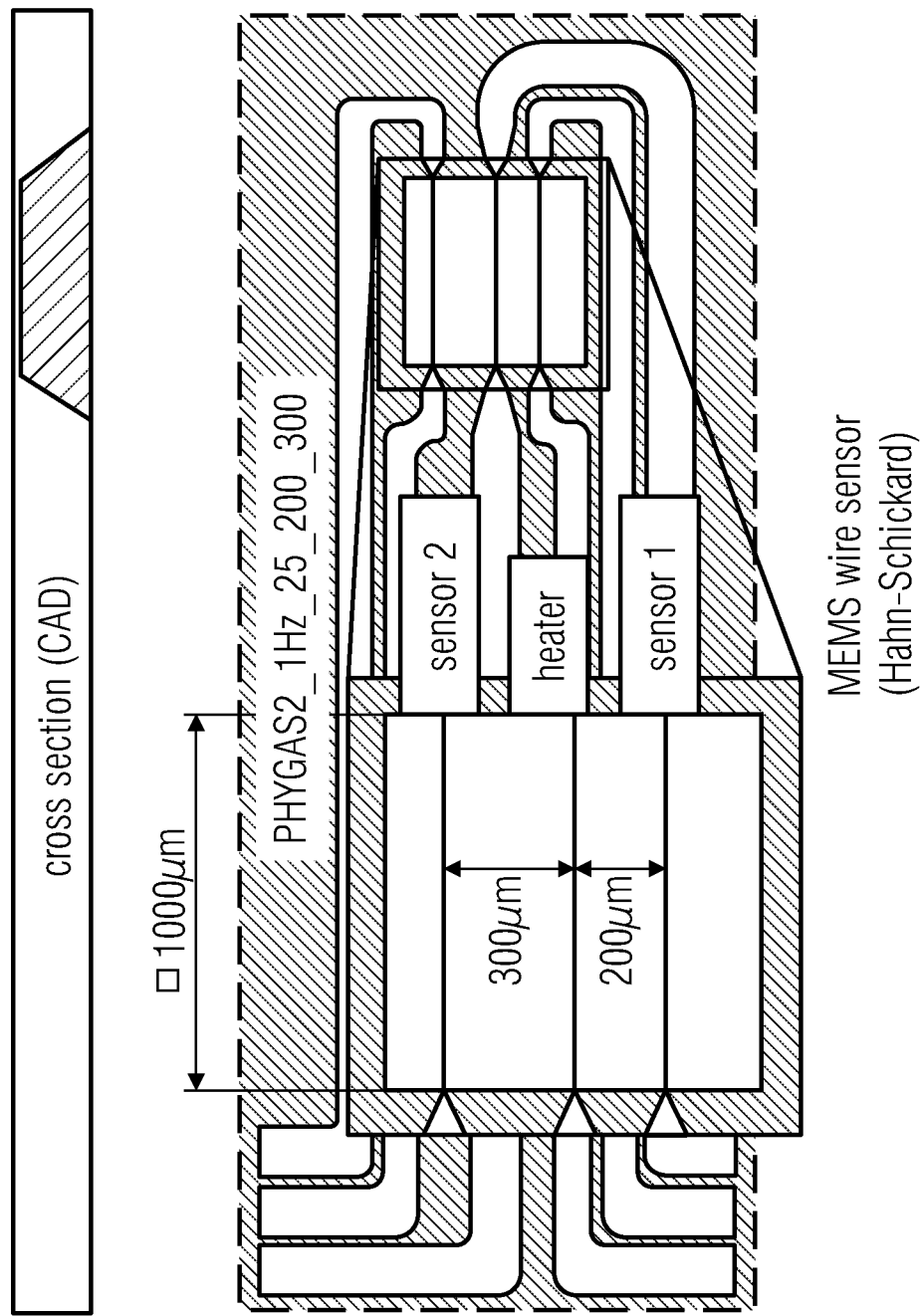
FIG. 21 shows an embodiment of an MEMS wire sensor (Hahn-Schickard)

The advantages of the same are:
infrared absorption at 4.3 μm wavelength, measurement of the concentration of $CO_2$ in the breathing gas by absorption
non-consuming
measurement in the main stream possible The disadvantages of the same are:
the mode of operation involves a respectively precise structure, expensive optic components
components are very sensitive to contamination by secretion and breath humidity
aging of the photodiode FIG. 21 shows an embodiment of an MEMS wire sensor (Hahn-Schickard)

The advantages of the same are:
small structure
physical measurement principle—non-consuming
cost effective
measurement in the steadied main stream possible The disadvantages of the same are:
in the predevelopment state—no product yet
measurement of the thermal gas characteristics heat conductivity and temperature conductivity: no real gas analysis, gas components have to be known
limited thermal resolution (0.2 vol % $CO_2$.

For capnometry, different portable devices for breathing gas analysis exist. Exemplarily, a product of Weinman Diagnostics is stated: a portable capnograph for $CO_2$ measurement and evaluation operating internally with an infrared sensor. The connection to the patient is established by a nasal cannula and the exhaled air will be guided to the device in the side stream through a long tube for determining the $CO_2$ content.

A further apparatus of that type is the CapnoTrue AMP offered by Bluepoint Medical, which operates in the main stream method with the IRMA Mainstream Analyzer by Phasein.

Different systems for patient respiration exist at the market. The same are differentiated according to the usage in the clinical and in the homecare field (e.g. systems of the companies Heinen+Löwenstein, Dräger and Stephan Medizintechnik). The systems of those suppliers include only in their top variations all measurement means for determining pressure, respiratory flow and breathing gas analysis. For this, several devices have to be combined that mostly measure remote from the patient.

The optional integration of both sensors ($CO_2$ and flow) into one sensor system can result in a significant reduction of the installation space and the system weight (a significant criterion for intubated patients). Only the measurement location close to the patient immediately at the mask or tube, as close as possible to the respiratory path, allows a significantly accurate measurement in order to prevent influences by tubes, movements or other sources of disturbance. Additionally, by the thermal measurement principle, more accurate flow measurements and a fast gas analysis are expected.

In the following, further embodiments and aspects of the invention will be described that can be used separately or in combination with further aspects or embodiments or features described herein.

An embodiment (aspect 1) relates to a miniaturized housing (package) for determining the concentration of gases, for example, for determining the $CO_2$ proportion in the expiration gas during expiration, which is configured as gas-tight measurement chamber with an opening for gas exchange via diffusion, sealed to the outside against leaking, which is configured as stack consisting of
a wiring carrier,
a barometric MEMS pressure sensor, advantageously (but not necessarily) a barometric altimeter with digital interface and (optionally) high A/D resolution (24 bit)
and a thermal MEMS gas sensor
wherein (optionally) heater and at least two detectors are cantilevered in the gas measurement space,
wherein (optionally) thermal gas response, barometric gas pressure and gas temperature are measured immediately at a measurement location in a very confined space and
(optionally) due to the mechanical separation between heater and detectors, heat transfer from heater to detectors mainly takes place via the measurement gas,
wherein (optionally) the detectors are arranged laterally from the heater at different defined distances to the same,
wherein (optionally) the heater of the thermal sensor is provided with a periodic heating power (120 Hz or more) and (optionally), the gas concentration-dependent amplitude and phase shift with respect to the heating signal is determined at the detectors,
wherein (optionally) the detector signals are compared absolutely and differentially both with respect to one another and with respect to the heater signal,
wherein (optionally) a synthesis of difference and sum formation is used for calibration to the gas type-dependent gas concentration ($CO_2$),
wherein (optionally), for pressure and temperature dependent drift correction, the values for absolute pressure and temperature determined with the barometric pressure sensor in the gas measurement space are calculated using polynomials,
wherein (optionally) the temperature resolution and absolute accuracy can be significantly increased via temperature calibration of the detectors of a thermal gas sensor and usage of their measurement signals,
wherein (optionally) the sensor housing comprises an inflow grid as mechanical protection,
wherein (optionally) the miniaturized sensor package (sensor housing) for determining the concentration of gases is arranged immediately behind a lateral bore at the flow tube,
wherein (optionally) the measurement gas is coupled out of the flow channel via diffusion through a bacteria or virus filter and
wherein (optionally) the concentration compensation takes place within 10 ms at normal breathing, since the volume of the gas measurement space is less than 250 $mm^3$ due to the miniaturized structure,
wherein (optionally) the miniaturized sensor package (sensor housing) is mechanically sealed against leakage to the flow tube via an elastic O-ring, a flat seal or via molded 2K plastic at the housing,
wherein (optionally) filter, geometry of the inflow grid and miniaturized gas measurement chamber provide a steadied area where the thermal sensor can operate undisturbed from outer flow,
wherein (optionally) the flow tube carrying the bacteria or virus filter can be configured as disposable,
wherein (optionally) the miniaturized sensor package (sensor housing) for determining the concentration of gases including its microprocessor-based signal evaluation only weighs several grams, has a small structural size and has, due to the usage of MEMS members, a lower power consumption, advantageously less than 50 mW and hence can be incorporated in mask, mouth piece or tracheal tube directly at the patient in order to enable exact and temporally undistorted measurement.

A further embodiment relates to an apparatus according to aspect 1 in combination with a second barometric altimeter which is outside the flow channel in the measurement device and detects the barometric air pressure of the room,
wherein the measurement device calculates, for example, the difference of the absolute pressure of the flow channel determined by the barometric MEMS pressure sensor in the miniaturized sensor package and the barometric pressure of the room, and hence, calculates the breathing pressure.

A further embodiment (aspect 3) relates to an apparatus according to aspect 1 or aspect 2 in combination with an MEMS flow sensor in the flow tube for measuring the breathing values in the main stream method,
wherein, for example with the help of the values for absolute pressure and gas temperature of the breathing air determined by the barometric MEMS pressure sensor in the miniaturized sensor package is converted from the mass flow measured by the MEMS flow sensor into the current volume flow at ATP conditions (ambient temperature and pressure).

A further embodiment (aspect 4) relates to an apparatus according to one of aspects 1 to 3, supplemented by a zero-point adjustment in connection with the flow signal of the flow sensor in the breath tube: dynamic calibration of the $CO_2$ sensor to fresh air or anesthetic gas concentrations of the respirator.

The thermal sensor has an increased signal dependence on the environmental influences absolute pressure and temperature. This means that if these parameters are not measured, wrong concentration values would be assumed for $CO_2$/or other gases. Therefore, the absolute pressure sensor is placed directly at the same measurement location (stack) which measures, apart from the barometric air pressure, at the same time the temperature.

During usage, there is the option that despite membrane (virus filter), small contaminations can settle at the detector wires of the sensor over a longer time period, whereby the signal might drift. The electronics also show an environment-dependent (mostly temperature-dependent) drift.

Therefore, it can be useful to adjust the sensor to its zero point when a known gas prevails. Frequently, fresh air, i.e. the air of the room is used for this. This is an advantageous procedure when switching on/setting up the sensor at a new patient or after changing the sensor. The sensor is taken out of its packaging, is electrically connected and subject to fresh air during initialization. At known air conditions (standard), the same calibrates itself. This procedure is common, both for heat wire anemometers (breathing gas measurement) as well as for capnometers (NDIR $CO_2$ measurement).

Thus, dynamic post-correction during respiration is possible (also an optional feature in embodiments of the invention): when the connected flow tube detects the end of the inspiration phase (the patient has been supplied with fresh air or fresh air enriched with anesthetic gas), the current measurement value of the sensor could be interpreted as zero-point for this known gas state and the sensor might be readjusted. (The anesthetic gas concentration out of the respirator is, for example, known to the respirator and is communicated to the spirometer device.

A reverse scenario would also be possible: due to errors in the patient tube system, the expired $CO_2$ is not correctly discharged and the $CO_2$ concentration (also in fresh air) increases critically: here no dynamic recalibration is allowed but an alarm has to be triggered due to the $CO_2$ concentration being too high during inspiration (fresh air measurement).

Due to the immediate geometric proximity of the measurement locations for flow and gas concentration, a flow signal and $CO_2$ signal run in a synchronous manner in this system. In that way, errors or readjustments can be corrected directly within one breathing.

In the still common side stream method of capnometry, gas is actively sucked off the main stream and reaches the capnometer in the respirator in the thin tubes across approximately 1.5 m. This results in a time offset between flow and $CO_2$ signal which is corrected on the software side/computer side. Only capnometers having direct irradiation of the breath flow tube (optical windows) measure time-synchronously to the flow signal.

According to a further aspect of the invention, decoupling into a closed chamber and gas diffusion through filters takes place.

According to a further aspect of the invention, embodiments have a low chamber gas volume which is particularly advantageous. Therefore, it becomes possible to represent a concentration-dependent dynamic signal at the sensor synchronously to the breathing cycle via diffusion.

According to one aspect, one or several of the following specifications for membrane and chamber (or for the sensor or the sensor arrangement in general) have to be considered:

The membrane in front of the sensor measurement chamber partitions the gas chamber into a steadied zone: the almost flow-free zone is an important prerequisite for thermal gas concentration measurement.

For some embodiments, it is important that the very low chamber volume in connection with the small diffusion time constant only allows dynamic concentration measurement. Finally, the gas exchange in the measurement chamber is a passive process and depends on the average free path length of the particles (see theoretical discussion of diffusion times above).

The membrane is (optionally) a hydrophobic virus/bacteria membrane additionally purchased, for example, from Millipore. The optional filter can prevent, for example, the entry of liquids into the measurement chamber.

The filter membrane diameters should not exceed the diameter of the breath flow tube, otherwise the filter sealing would have to be implemented beyond the contours/edges of the tube and would no longer be a planar area. Thereby, the contact pressure between tube and device would have to be increased, since the chamber is to be connected to the breath tube in a gas-tight (leakage-free) manner. A good choice is, for example, 60% of the outer breath tube diameter.

Since the filter contaminates during use it is (optionally) part of the disposable breath tube: thus, defined diffusion constants are obtained in a new tube. The gas sensor placed in the reusable device carries a grid as mechanical protection so that the filter does not bend into the measurement space in an uncontrolled manner and corrupts the result (mechanically supporting the filter membrane at overpressure/cough, preventing uncontrolled tearing). The sensor grid itself can also carry a filter membrane preventing entry of disinfectant solution into the measurement space during wet sterilization of the device. (This additional membrane has to be considered during gas exchange/dimensioning).

The seal can be established either on the side of the housing around the sensor (current solution with O-ring seal) or by a sealing lip molded to the disposable tube/adhered with the filter or both.

The mechanical (plug) connection of the breath tube and the device should ensure that there are no leaks between tube and measurement chamber.

The membrane serves (optionally) to separate bacterial/virus contamination of the reusable device out of the breathing gas, but simultaneously protects the sensor from the entry of liquids (precipitating humidity, sputum).

The membrane generally serves as bacteria/virus filter

The measurement volume is relatively small in embodiments

The sensor as a whole is also relatively small.

According to one aspect, not only an average value of the $CO_2$ concentration can be measured, but also a dynamic change as needed in breathing gas analysis.

Figure 22:
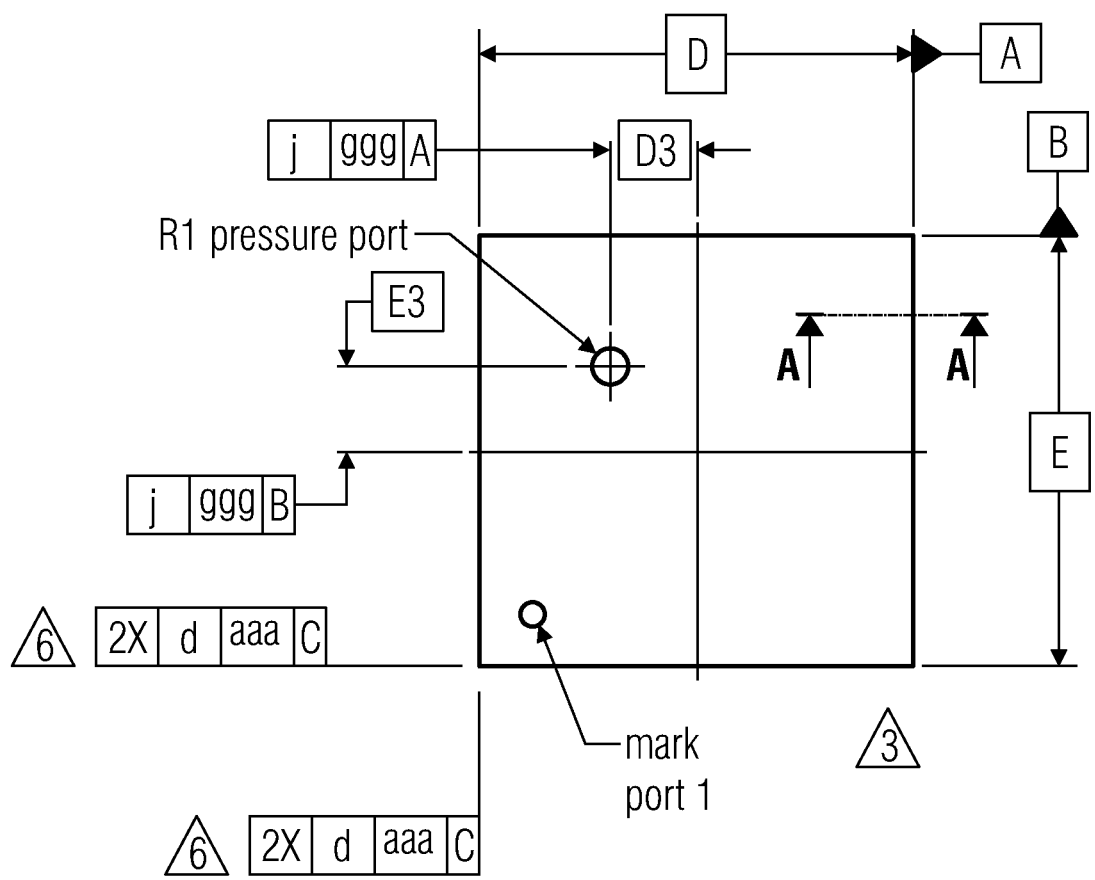
FIG. 22 shows a sensor of the type LPS25H from STMicroelectronics.

According to one aspect, the pressure sensor is, for example, a sensor of the type LPS25H from the producer STMicroelectronics as shown in FIG. 22. Here, in top view, an R1 pressure port and a mark Pin1 of port 1 is shown. However, any barometric pressure sensor, whose geometrical dimensions are suitable for structuring the sensor arrangement and whose measurement frequency, measurement resolution and accuracy is within the requested range can be used.

Figure 23:
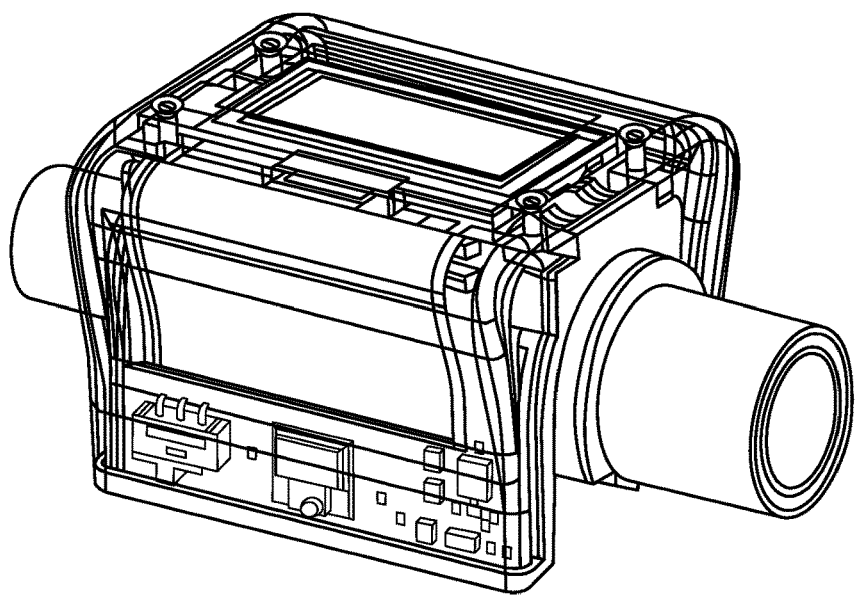
FIG. 23 shows a further embodiment and optional features.
Figure 24:
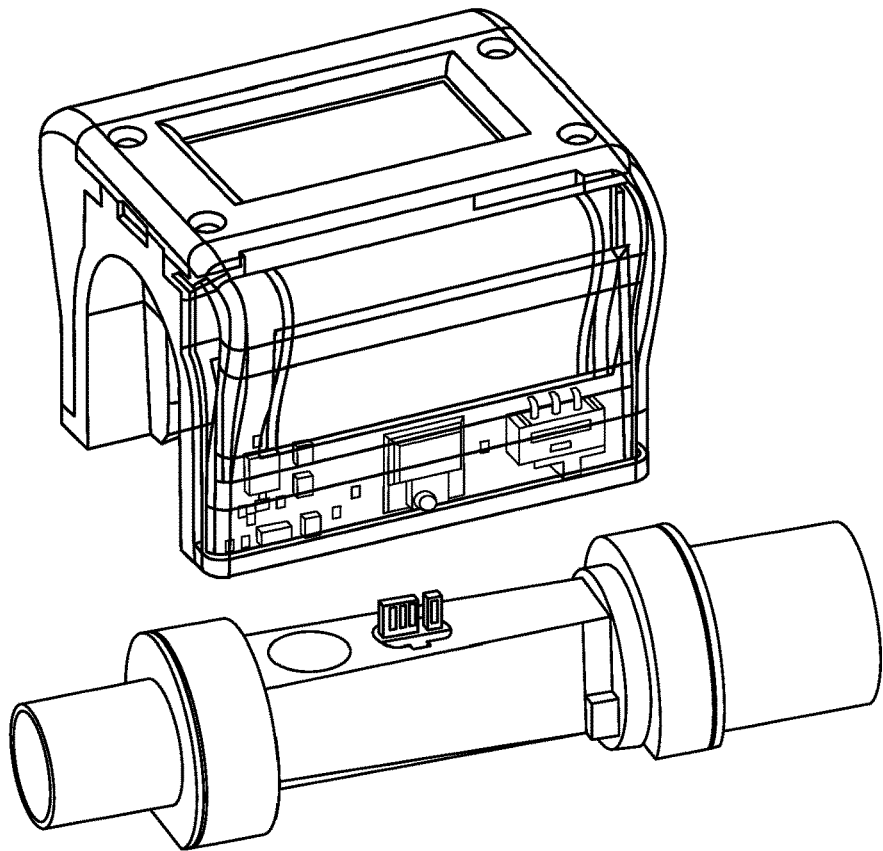
FIG. 24 shows a further embodiment and optional features.

FIGS. 23 and 24 show further embodiments and optional features, such as:
separation in reusable device and breathing channel as disposable product for single use (for example tube and flow sensor as disposables)
measurement of flow, pressure, temperature and $CO_2$
dealing with breathing dynamics and humidity
communication via Bluetooth or USB stream FIGS. 25 and 26 show further embodiments with regard to an inventive system architecture (details optional).

Figure 27:
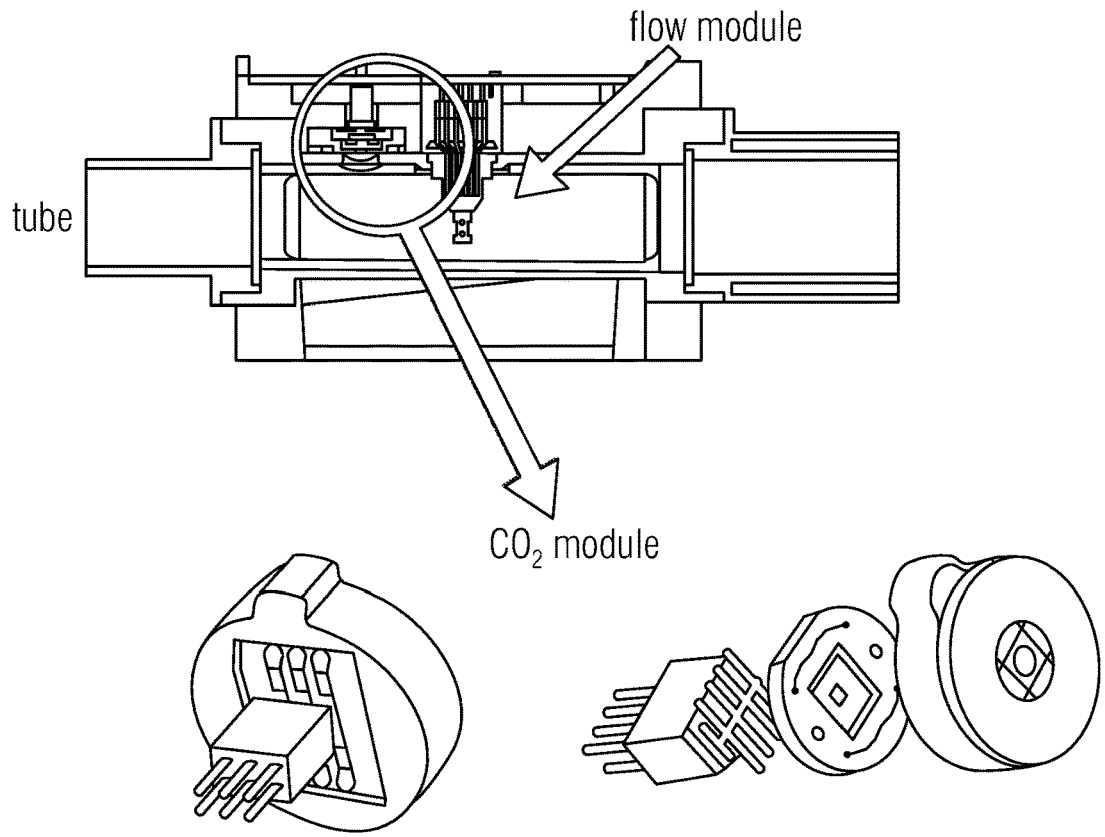
FIG. 27 shows a further embodiment with regard to further exemplary apparatuses in a modular structure.
Figure 28:
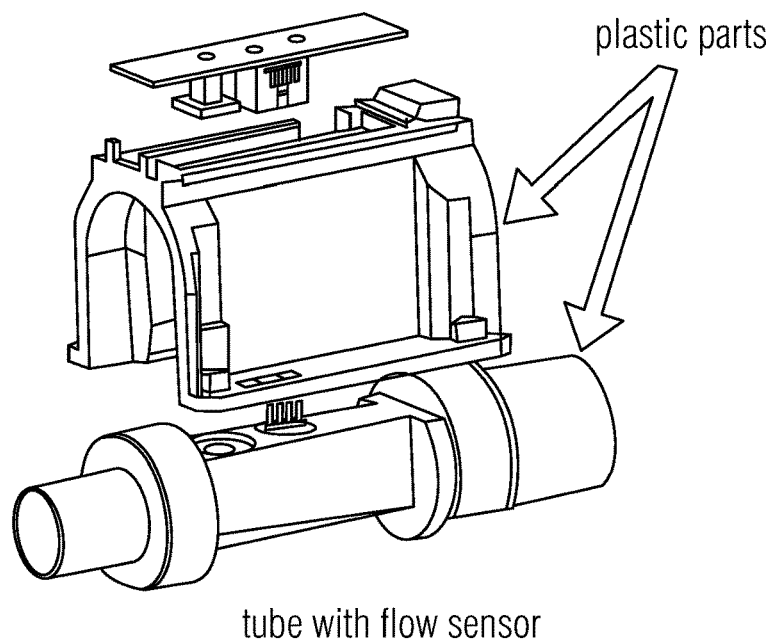
FIG. 28 shows a further embodiment with regard to further exemplary apparatuses in a modular structure.

FIGS. 27 and 28 show further embodiments with regard to further exemplary apparatuses in a modular structure.

Figure 29:
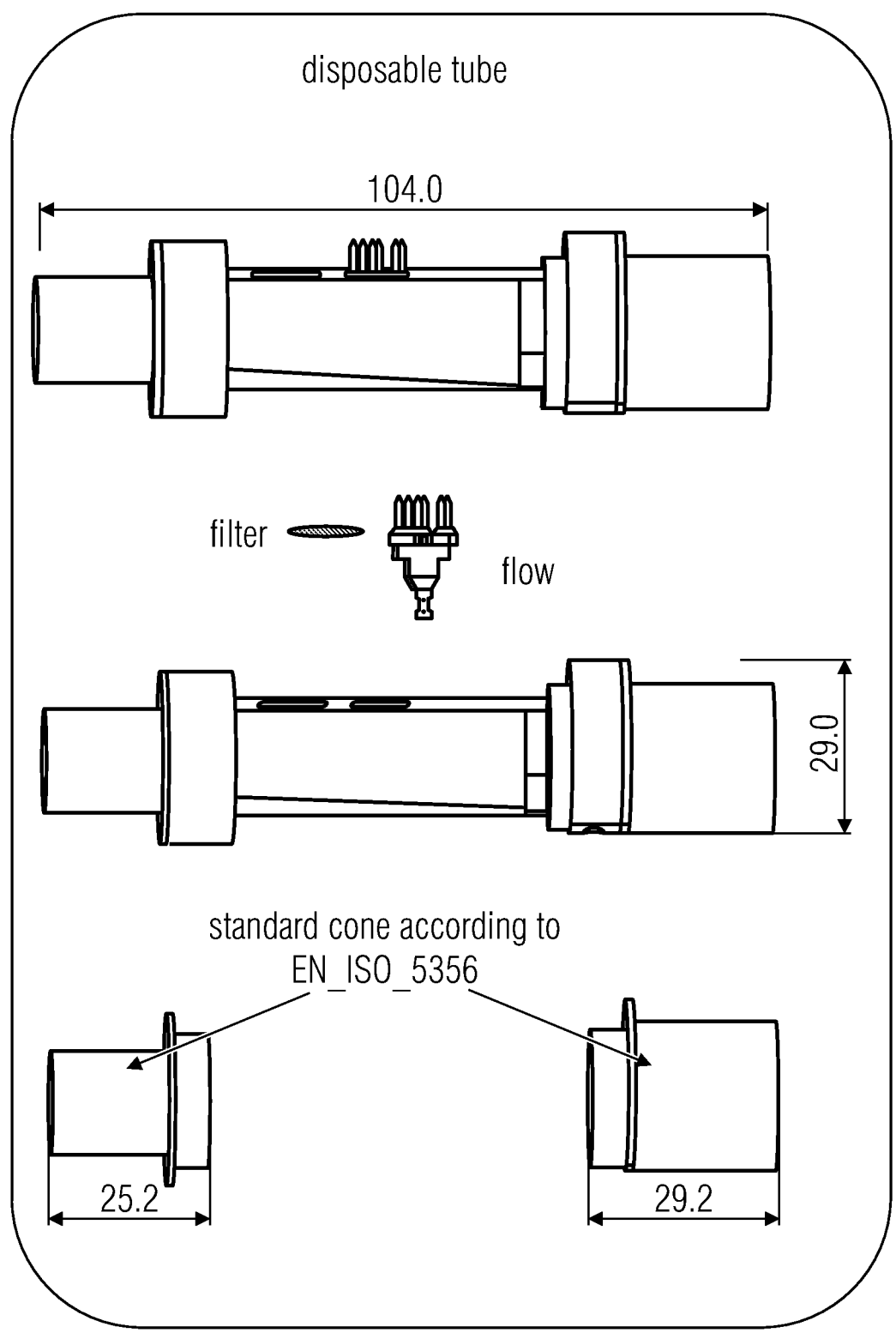
FIG. 29 shows a disposable tube of a multisensor platform for measurement of $CO_2$ concentration and volume flow of breathing air close to the patient.

FIG. 29 exemplarily shows a disposable tube of a multisensor platform for measurement of $CO_2$ concentration and volume flow of breathing air close to the patient.

Figure 30:
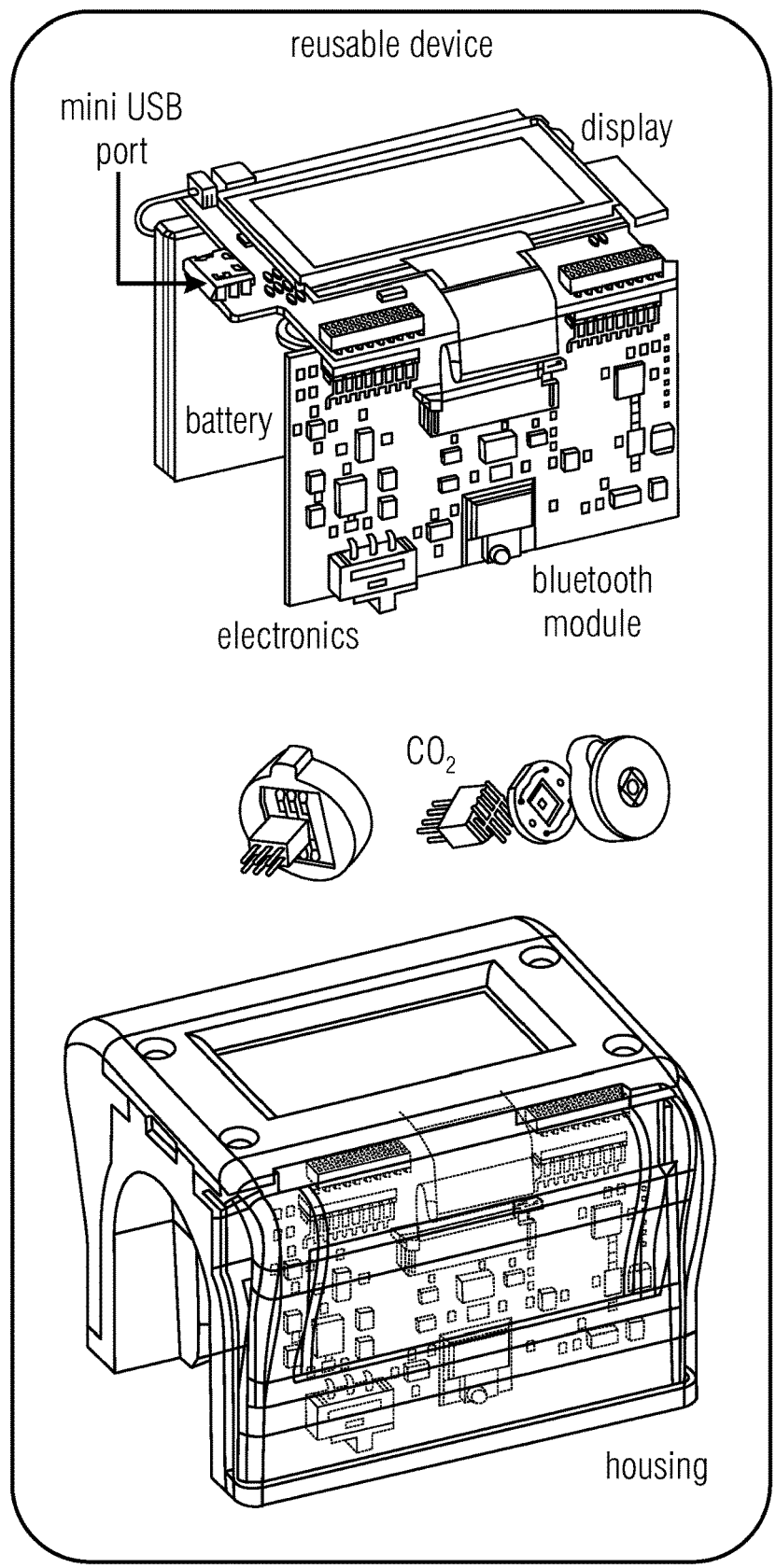
FIG. 30 shows an embodiment of a reusable device.
Figure 31:
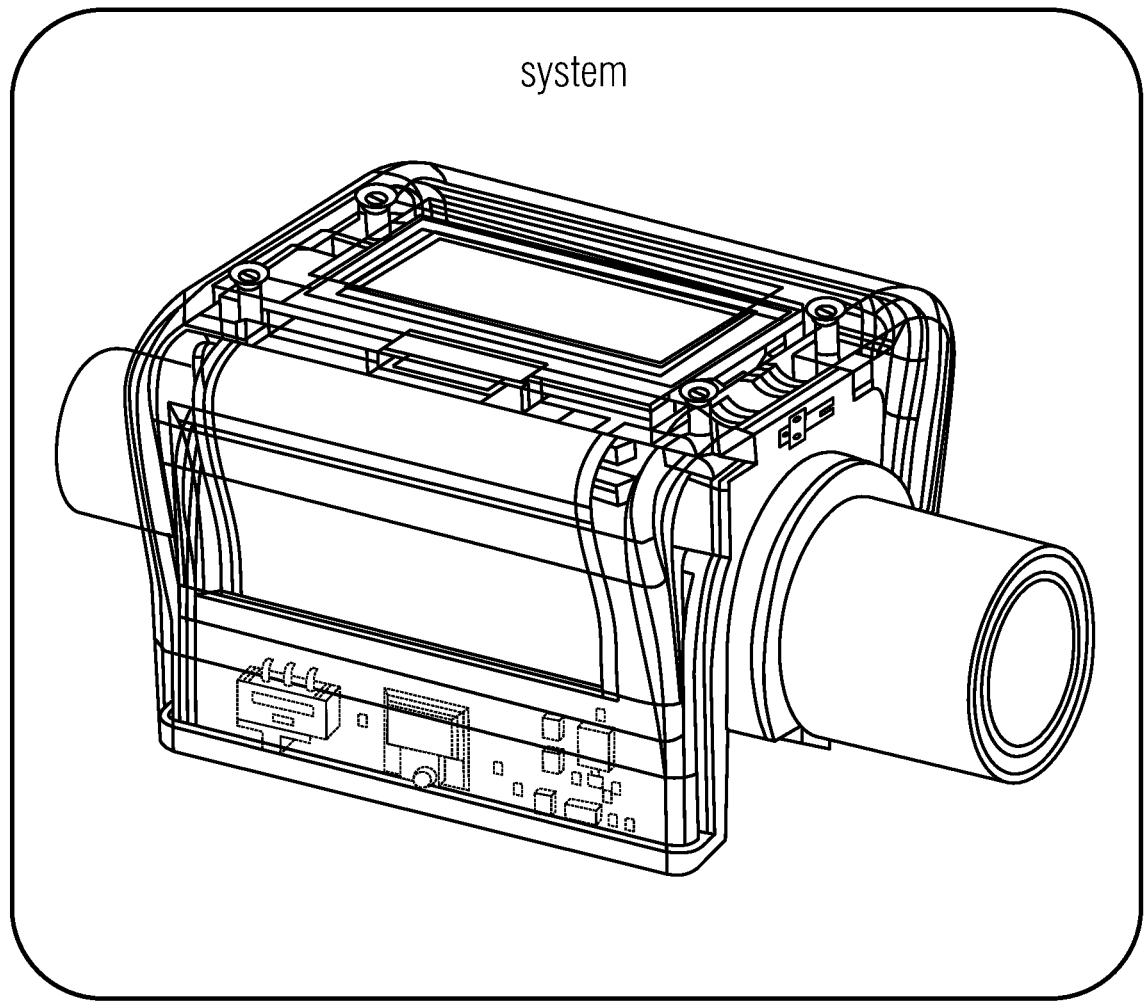
FIG. 31 shows the reusable device coupled onto a disposable tube of a multisensor platform for measurement of $CO_2$ concentration and volume flow of the breathing air close to the patient.

FIG. 30 shows an embodiment of a reusable device coupled in FIG. 31 onto a disposable tube of a multisensor platform for measurement of $CO_2$ concentration and volume flow of the breathing air close to the patient.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. Sensor arrangement, comprising:
a barometric pressure sensor; and
a thermal gas sensor;
wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor;
wherein the thermal gas sensor comprises a frame that is arranged on the barometric pressure sensor and
wherein the frame is configured to carry the gas-permeable measurement structure such that the active areas of the gas-permeable measurement structure span a free inner area of the thermal gas sensor surrounded by the frame;
wherein the gas inlet opening of the barometric pressure sensor or the pressure-sensitive surface of the barometric pressure sensor borders on the free inner area of the thermal gas sensor.

2. Sensor arrangement according to claim 1, wherein the thermal gas sensor comprises at least three electric conductor structures, wherein the electric conductor structures are spaced apart by gaps, wherein a first electric conductor structure is configured to be provided with a heating signal and wherein a second electric conductor structure and a third electric conductor structure are arranged at different distances to the first electric conductor structure, and wherein the second electric conductor structure and the third electric conductor structure are configured to operate as temperature sensors.

3. Sensor arrangement according to claim 2, wherein the electric conductor structures are crystalline silicon wires or wherein the electric conductor structures are a polycrystalline heater on a membrane material as well as semiconductor temperature detectors or thermostacks.

4. Sensor arrangement according to claim 1, wherein the thermal gas sensor comprises at least two electric conductor structures, wherein the electric conductor structures are spaced apart by at least one gap, wherein a first electric conductor structure is configured to be provided with a heating signal and wherein a second electric conductor structure is configured to operate as temperature sensor.

5. Sensor arrangement according to claim 4, wherein the sensor arrangement is configured to provide the first conductor structure with a heating signal in a first time interval and to use the second conductor structure as temperature sensor, and
 wherein the sensor arrangement is configured to provide the second conductor structure with a heating signal in a second time interval and to use the first conductor structure as temperature sensor.

6. Sensor arrangement according to claim 1, wherein the thermal gas sensor comprises at least three electrically conductive ridges, wherein the ridges are spaced apart by gaps, wherein a metallization or doping of a first ridge is configured to be provided with the heating signal and wherein a second and a third ridge are arranged asymmetrically with respect to the first ridge and wherein metallizations or dopings of the second ridge and the third ridge are configured to operate as temperature sensors.

7. Sensor arrangement according to claim 2, wherein the electric conductor structures or wires or ridges are configured to be surrounded by a gas to be analyzed and wherein the first electric conductor structure or the first wire or the first ridge are configured to allow heat transfer via the gas to be analyzed to the second electric conductor structure or to the second wire or to the second ridge and to the third electric conductor structure or to the third wire or to the third ridge, and wherein the second and third electric conductor structures or wires or ridges are configured to serve as sensors for the heat transfer.

8. Sensor arrangement according to claim 1, wherein the thermal gas sensor comprises a carrier material,
 wherein the thermal gas sensor comprises a continuous recess in a central area extending from a surface of the thermal gas sensor facing away from the barometric pressure sensor up to a surface of the thermal gas sensor facing the barometric pressure sensor and
 wherein the gas-permeable measurement structure is arranged in an area of the recess.

9. Sensor arrangement according to claim 1, wherein the thermal gas sensor is connected to the barometric pressure sensor by means of an adhesive, such that the adhesive is not in contact with the gas inlet opening of the barometric pressure sensor or with the pressure-sensitive surface of the barometric pressure sensor.

10. Sensor arrangement according to claim 1, wherein the sensor arrangement comprises a printed circuit board material;
 wherein the barometric pressure sensor and on top of the same the thermal gas sensor are arranged on one side of the printed circuit board material and wherein a plug or solder contact for electric contacting are arranged on another side of the printed circuit board material facing away from the pressure sensor and the thermal gas sensor, or
 wherein the barometric pressure sensor and on top of the same the thermal gas sensor are arranged in a recess of the printed circuit board material and wherein a plug for electric contacting is arranged on a side of the printed circuit board material.

11. Sensor arrangement according to claim 1, wherein the sensor arrangement comprises an evaluator, wherein the evaluator is configured to determine a gas concentration based on phase and amplitude of sensor signals acquired by using the gas sensor and in dependence on pressure information provided the barometric pressure sensor and possibly temperature information.

12. Sensor arrangement according to claim 1, wherein the sensor arrangement is surrounded by a housing providing a volume within the same where the sensor arrangement resides,
 wherein the housing comprises a housing opening through which a gas to be analyzed can reach the sensor arrangement within the volume from an outside of the housing by a diffusion process,
 wherein the opening of the housing comprises a membrane that is configured to protect the sensor arrangement from contamination and wherein the membrane is configured to allow diffusion of a gas to be analyzed.

13. Sensor apparatus, comprising:
 a flow channel,
 wherein the flow channel comprises an opening in a wall; and
 a sensor arrangement according to claim 1, wherein the sensor arrangement is arranged such that the sensor arrangement is spatially connected to the inside of the flow channel through the opening to allow gas exchange between the inside of the flow channel and the sensor arrangement.

14. Sensor apparatus according to claim 13, wherein the sensor apparatus is configured such that the frame seals a gas measurement space of the opening of the housing to the outside, wherein a time period up to a compensation of the gas concentration in the area of the gas sensor deviating by at most 0.5 vol % from the gas concentration in the flow channel is less than 10 ms.

15. Sensor apparatus according to claim 13, wherein the sensor apparatus is configured such that a chamber comprised in the sensor arrangement represents an area with steadied flow.

16. Sensor apparatus according to claim 13, wherein a sensor apparatus comprises a flow sensor, wherein the flow sensor is arranged to be able to determine a flow velocity and/or a gas mass flow and/or a volume flow in the flow channel.

17. Sensor apparatus according to claim 13, wherein the sensor apparatus comprises a second barometric pressure sensor that is configured to measure an environmental pressure.

18. Sensor apparatus according to claim 13, wherein the sensor apparatus is configured to detect, based on information on a flow velocity of fresh air or fresh air enriched with anaesthetic gas in the flow channel and/or based on information on a flow direction of fresh air or fresh air enriched with anaesthetic gas in the flow channel, a time for calibration and to perform calibration of the thermal gas sensor in response thereto.

19. Sensor arrangement, comprising:
 a barometric pressure sensor; and a thermal gas sensor;
wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor;
wherein the thermal gas sensor comprises a carrier material,
wherein the thermal gas sensor comprises a continuous recess in a central area extending from a surface of the thermal gas sensor facing away from the barometric pressure sensor up to a surface of the thermal gas sensor facing the barometric pressure sensor and
wherein the gas-permeable measurement structure is arranged in an area of the recess.

20. Sensor arrangement, comprising:
a barometric pressure sensor; and
a thermal gas sensor;
wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor;
wherein the thermal gas sensor is connected to the barometric pressure sensor by means of an adhesive, such that the adhesive is not in contact with the gas inlet opening of the barometric pressure sensor or with the pressure-sensitive surface of the barometric pressure sensor.

21. Sensor arrangement, comprising:
a barometric pressure sensor; and
a thermal gas sensor;
wherein the thermal gas sensor is arranged on the barometric pressure sensor or beside the barometric pressure sensor such that a gas-permeable measurement structure of the thermal gas sensor is arranged in front of a gas inlet opening of the barometric pressure sensor or in front of a pressure-sensitive surface of the barometric pressure sensor;
wherein the sensor arrangement comprises a printed circuit board material;
wherein the barometric pressure sensor and on top of the same the thermal gas sensor are arranged on one side of the printed circuit board material and wherein a plug or solder contact for electric contacting are arranged on another side of the printed circuit board material facing away from the pressure sensor and the thermal gas sensor, or
wherein the barometric pressure sensor and on top of the same the thermal gas sensor are arranged in a recess of the printed circuit board material and wherein a plug for electric contacting is arranged on a side of the printed circuit board material.

\* \* \* \* \*